(12) United States Patent
Iida et al.

(10) Patent No.: US 8,044,219 B2
(45) Date of Patent: Oct. 25, 2011

(54) AMINO GROUP-CONTAINING HETEROCYCLIC DERIVATIVES AND SENSITIZING DYES FOR PHOTOELECTRIC CONVERSION CONTAINING THE HETEROCYCLIC DERIVATIVES

(75) Inventors: Katsumi Iida, Chigasaki (JP); Etsuya Kawata, Chigasaki (JP); Shoji Watanabe, Chigasaki (JP); Kana Kobayashi, Chigasaki (JP)

(73) Assignee: AGC Seimi Chemical., Ltd., Chigasaki-shi (JP)

( * ) Notice: Subject to any disclaimer, the term of this patent is extended or adjusted under 35 U.S.C. 154(b) by 1015 days.

(21) Appl. No.: 11/914,344

(22) PCT Filed: Apr. 28, 2006

(86) PCT No.: PCT/JP2006/308977
§ 371 (c)(1),
(2), (4) Date: Nov. 13, 2007

(87) PCT Pub. No.: WO2006/120939
PCT Pub. Date: Nov. 16, 2006

(65) Prior Publication Data
US 2009/0025781 A1  Jan. 29, 2009

(30) Foreign Application Priority Data
May 13, 2005 (JP) ................. 2005-141090

(51) Int. Cl.
C07D 333/04 (2006.01)
H01L 31/04 (2006.01)
(52) U.S. Cl. ............... 549/77; 549/50; 549/59; 136/252
(58) Field of Classification Search .............. 136/252; 549/50, 59, 77
See application file for complete search history.

(56) References Cited

FOREIGN PATENT DOCUMENTS
JP         2 288874        11/1990
(Continued)

OTHER PUBLICATIONS
Yagi et al. "Photofunctional . . . . . " CA141:164771 (2004).*
(Continued)

*Primary Examiner* — Celia Chang
(74) *Attorney, Agent, or Firm* — Oblon, Spivak, McClelland, Maier & Neustadt, L.L.P.

(57) ABSTRACT

It is intended to provide novel amino group-containing heterocyclic derivatives, which have a broad absorption zone in the visible region and are suitable for sensitizing dyes for photoelectric conversion having a high photoelectric conversion efficiency, and photoelectric conversion materials, photoelectric conversion electrodes and photoelectric conversion cells using the same. Namely, a heterocyclic derivative represented by the following general formula (I) and containing an amino group at the terminus:

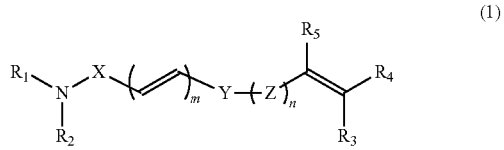

(1)

wherein $R_1$, $R_2$, $R_4$ and $R_5$ independently represent each a hydrogen atom or a monovalent organic group optionally having one or more substituent; $R_3$ represents an anchor group capable of binding to an inorganic porous material showing semiconductor characteristics; X represents a divalent aromatic hydrocarbon group or a combination of two or more aromatic hydrocarbons being divalent or higher; Y represents a divalent aromatic heterocyclic group having a sulfur atom; Z represents a divalent aromatic heterocyclic group, a divalent aromatic hydrocarbon group, a divalent unsaturated hydrocarbon group or a combination thereof; and m is an integer of from 1 to 3.

12 Claims, 1 Drawing Sheet

FOREIGN PATENT DOCUMENTS

| | | |
|---|---|---|
| JP | 8 339001 | 12/1996 |
| JP | 2004 143355 | 5/2004 |
| JP | 2005 15750 | 1/2005 |
| JP | 2005 32475 | 2/2005 |
| JP | 2005 97561 | 4/2005 |
| JP | 2006 111783 | 4/2006 |
| WO | 02 11213 | 2/2002 |
| WO | 2004 063283 | 7/2004 |

OTHER PUBLICATIONS

Stenger et al. "Main- chain syndioregic. . . . . " CA133:208257 (2000).*

Breitung et al. "Thiazole . . . . . " J. Am. Chem. Soc. 122 p. 1154-1160 (2000).*

Tian et al. "Low-cost dyes . . . . . " CA153:363609 (2010).*

King "bioisosteres . . . . . " Med. Chem. Principle and Practice (1994) o.206-209.*

Kobmehl et al. "Uber polyarylene . . . . " Makromol. Chem. 183 p. 2747-2769 (1982).*

O'Regan, et al., "A Low-cost, high-efficiency solar cell based on dye-sensitized colloidal $TiO_2$ films", Letters to Nature, vol. 353, pp. 737-740, 1991.

* cited by examiner

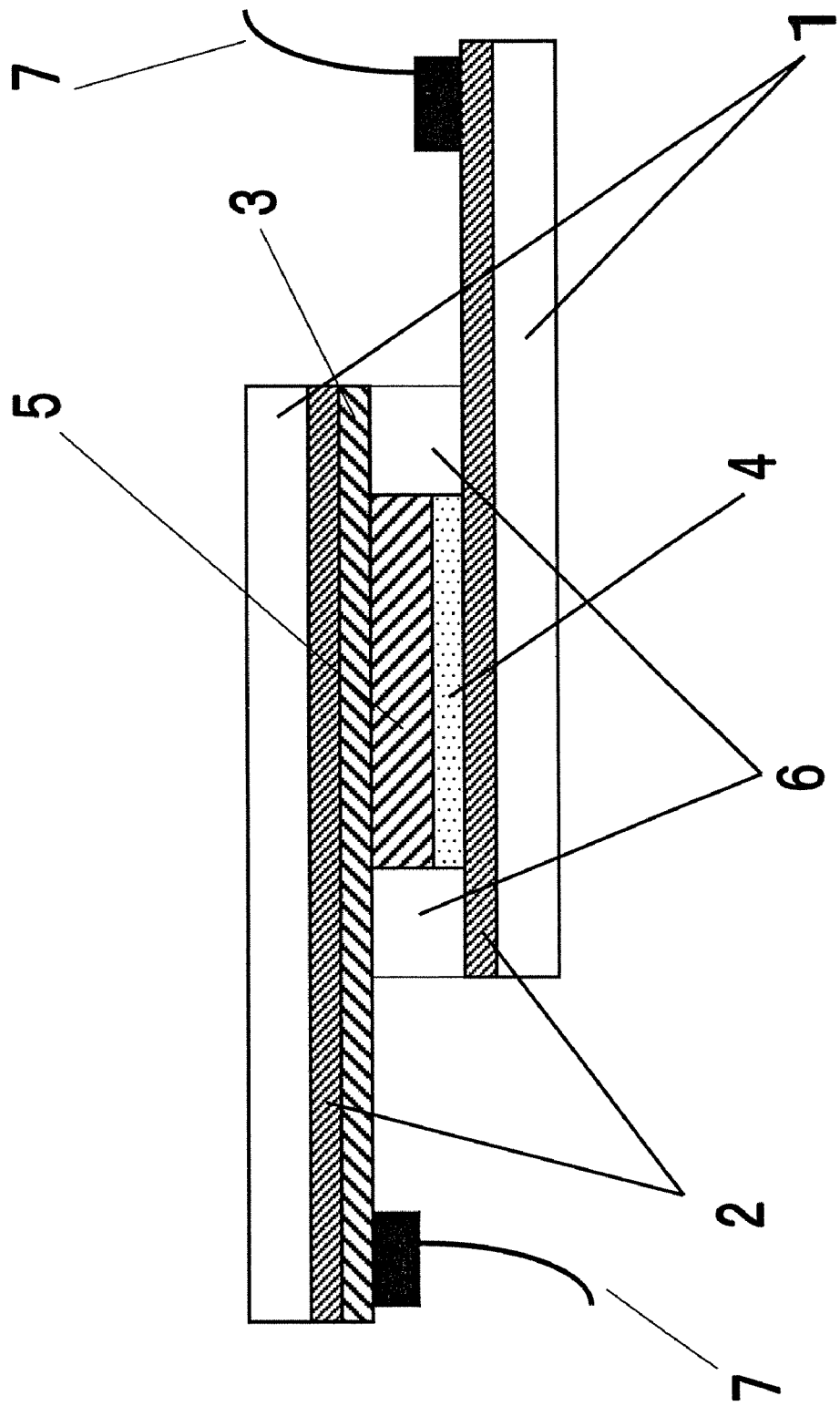

AMINO GROUP-CONTAINING HETEROCYCLIC DERIVATIVES AND SENSITIZING DYES FOR PHOTOELECTRIC CONVERSION CONTAINING THE HETEROCYCLIC DERIVATIVES

CROSS-REFERENCE TO RELATED APPLICATIONS

The present application is a 35 U.S.C. §371 National Stage patent application of International patent application PCT/JP06/308977, filed on Apr. 28, 2006, which claims priority to Japanese patent application JP 2005-141090, filed on May 13, 2005.

TECHNICAL FIELD

The present invention relates to novel amino group-containing heterocyclic derivatives, sensitizing dyes for photoelectric conversion (photovoltaic conversion) which use such heterocyclic derivatives, photovoltaic materials which use such sensitizing dyes, photovoltaic electrodes which use such photovoltaic materials, and photovoltaic solar cells which use such photovoltaic electrodes.

BACKGROUND ART

Currently, energy is largely dependent on fossil fuels such as petroleum, coal and natural gas, but the future depletion of fossil fuels is a serious concern. Also, when energy is obtained from fossil fuels, carbon dioxide discharge inevitably occurs. Such discharge imposes a large burden on the environment, and is thus regarded as a major problem.

Recently, owing to such concerns, more attention is being paid to photovoltaic power generation, with active development work currently being carried out on, for example, silicon solar cells that use crystalline (single-crystal or polycrystalline) silicon or amorphous silicon, and on compound semiconductor solar cells which use gallium and arsenic. However, because production costs and other problems remain to be overcome, photovoltaic power generation still lacks widespread applicability. At the same time, numerous disclosures have been made concerning solar cells which use photosensitizing dyes, but such dyes have had a low conversion efficiency and a poor durability.

This was the situation in the art when Gratzel et al. published a report in 1991 (Non-Patent Document 1) describing a photovoltaic electrode and a photovoltaic cell that use an inorganic semiconductor porous material photosensitized with a dye. The photovoltaic device in their report is manufactured using a relatively inexpensive inorganic oxide semiconductor such as titanium oxide, and enables photovoltaic devices to be obtained at a lower cost than general-purpose silicon solar cells. However, it is not currently possible to achieve a high photovoltaic conversion efficiency without the use of a ruthenium-based sensitizing dye. Owing to the high cost of such dyes and the low crystal abundance of ruthenium, significant challenges remain to be overcome before a stable supply of such photovoltaic devices can be established. Active development efforts are also being carried out on organic dyes, although these have not yet reached a practical stage owing in part to their low conversion efficiency. Dyes with specific acrylic acid sites and sensitizing dyes having amide derivatives have also been developed (see Patent Documents 1, 2 and 3), but fall short in terms of performance.

Patent Document 1: JP 2002-011213 A
Patent Document 2: JP 2004-143355 A
Patent Document 3: JP 2005-097561 A
Non-Patent Document 1: Brian O'Regan and Michael Gratzel, "A low-cost, high-efficiency solar cell based on dye-sensitized colloidal TiO$_2$ films," Nature 353, 737-740 (October 1991; Great Britain).

DISCLOSURE OF THE INVENTION

Problems to be Solved by the Invention

Accordingly, an object of the invention is to provide a novel amino group-containing heterocyclic derivative which is useful as a sensitizing dye for photovoltaic conversion that has a broad absorption band in the visible range and can be used in dye-sensitized photovoltaic cells. Further objects of the invention are to provide a photovoltaic material in which such a sensitizing dye for photovoltaic conversion is attached to an inorganic porous material having semiconductor characteristics, a photovoltaic electrode which is obtained by forming a layer of such a photovoltaic material on a transparent electrode, and a photovoltaic cell which includes such a photovoltaic electrode, an electrolyte layer and an electrically conductive counterelectrode.

Means for Solving the Problems

As a result of extensive investigations, the inventors have discovered that compounds having a specific partial structure are useful as sensitizing dyes for photovoltaic conversion. That is, the invention provides a heterocyclic derivative which has a terminal amino group and is of general formula (1) below.

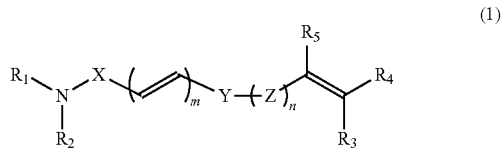

In general formula (1), $R_1$, $R_2$, $R_4$ and $R_5$ are each independently a hydrogen atom or a monovalent organic residue which may have one or more substituent thereon. $R_1$ and $R_2$ may together form a ring. Alternatively, $R_1$ and/or $R_2$ may form a ring together with X.

$R_3$ is an anchoring group which is capable of attaching to an inorganic porous material having semiconductor characteristics.

X is a divalent aromatic hydrocarbon group or a combination of two or more divalent aromatic hydrocarbon groups, which divalent aromatic hydrocarbon group may have one or more substituent and may be condensed from two or more rings.

Y is a divalent aromatic heterocyclic group having a sulfur atom. The divalent aromatic heterocyclic group may have one or more substituent and may be condensed from two or more rings.

Z is a divalent aromatic heterocyclic group, a divalent aromatic hydrocarbon group, a divalent unsaturated hydrocarbon group or a combination thereof. The divalent aromatic heterocyclic group, divalent aromatic hydrocarbon group and divalent unsaturated hydrocarbon group may have one or more substituent. The divalent aromatic heterocyclic group and divalent aromatic hydrocarbon group may be condensed from two or more rings.

The structure from X to the anchoring group $R_3$ forms a π-conjugated system.

The letter m is an integer from 1 to 3, and the letter n is the integer 0 or 1. The double bonds in formula (1) may allow the formation of any cis-trans isomer configuration.

X in above general formula (1) is preferably a phenylene, naphthylene, anthrylene, phenanthrylene, biphenylene or terphenylene group, any of which may have one or more substituent thereon.

In above formula (1), $R_3$ is preferably a carboxyl, phosphoric acid or sulfonic acid group.

Also, in formula (1), it is preferable for $R_1$, $R_2$, $R_4$ and $R_5$ to be each independently a hydrogen atom, an aliphatic hydrocarbon, aromatic hydrocarbon or aromatic heterocyclic group which may have one or more substituent thereon, a halogen atom, a cyano, isocyano, thiocyanate group, isothiocyanate, nitro, hydroxyl, mercapto, amino or amide group, or a group of general formula (2) below

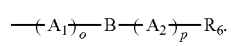  (2)

In above general formula (2), $A_1$ and $A_2$ are each independently O, NH or S; B is carbonyl, thiocarbonyl, sulfinyl or sulfonyl; the letters o and p are each independently 0 or 1; and $R_6$ is a hydrogen atom, a monovalent aliphatic hydrocarbon, aromatic hydrocarbon or aromatic heterocyclic group, any of which may have one or more substituent thereon, a halogen atom, or a cyano, isocyano, thiocyanate, isothiocyanate, nitro, hydroxyl, mercapto, amino or amide group.

$R_4$ in above general formula (1) is preferably an electron-withdrawing group, and more preferably a cyano, ester, amide or perfluoroalkyl group.

In above general formula (1), $R_3$ is preferably a carboxyl group.

Y in above general formula (1) is preferably a 2,5-thienylene group or a 2,5-thienothienylene group, either of which may have one or more substituent.

X in above general formula (1) is preferably a phenylene group which may have one or more substituent.

In one preferred embodiment, the letter n in above general formula (1) represents 0.

In another preferred embodiment, the letter n in above general formula (1) represents 1.

Z in general formula (1) is preferably a 2,5-thienylene group or a 2,5-thienothienylene group, either of which may have one or more substituent.

X in general formula (1) is preferably a 1,4-phenylene group substituted with one or more fluorine atom.

The invention also provides a sensitizing dye for photovoltaic conversion which includes the above-described terminal amino group-containing heterocyclic derivative of general formula (1).

The foregoing sensitizing dye for photovoltaic conversion may further include a photosensitizing dye other than the terminal amino group-containing heterocyclic derivative of general formula (1).

The invention additionally provides a photovoltaic material which is formed by attaching the above sensitizing dye for photovoltaic conversion to an inorganic porous material having semiconductor characteristics.

The above inorganic porous material which exhibits semiconductor characteristics is preferably composed of an inorganic oxide.

The invention further provides a photovoltaic electrode which is obtained by forming a layer of the above photovoltaic material on a transparent electrode.

The invention provides as well a photovoltaic cell which includes the above photovoltaic electrode, an electrolyte layer, and an electrically conductive counterelectrode.

Effects of the Invention

The amino group-containing heterocyclic derivative of the invention, by having a specific partial structure, possesses a broad absorption band in the visible region, thus enabling its use as an optical functional material, especially as a sensitizing dye for photovoltaic conversion. In particular, by using such a dye in a dye-sensitized photovoltaic cell, a highly stable photovoltaic cell can be obtained.

Moreover, by selecting specific substituents, the HOMO and LUMO energy levels can be easily tuned, enabling the desired performance in combination with the other materials making up the dye-sensitized photovoltaic cell to be achieved.

BRIEF DESCRIPTION OF THE DIAGRAM

FIG. 1 is a schematic view of a photovoltaic cell test specimen used in the photovoltaic conversion tests carried out in the subsequently described examples of the invention.

LEGEND

1: Glass substrates
2: Transparent electrode layers
3: Platinum electrode layer
4: Titanium oxide porous layer (to which the sensitizing dye for photovoltaic conversion has been adsorbed)
5: Electrolyte
6: Spacers made of plastic film
7: Measurement leads

BEST MODE FOR CARRYING OUT THE INVENTION

The invention is described more fully below.

In the present specification, when it is stated that an entity "may have one or more substituent thereon," the substituent is exemplified by aliphatic hydrocarbon groups, aromatic hydrocarbon groups, aromatic heterocyclic groups, halogen atoms, cyano, isocyano, thiocyanate, isothiocyanate, nitro, hydroxyl, mercapto, amino and amide groups, and monovalent groups of general formula (2) below.

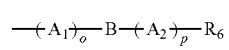  (2)

In above general formula (2), $A_1$ and $A_2$ are each independently O, NH or S; B is carbonyl, thiocarbonyl, sulfinyl or sulfonyl; the letters o and p are each independently 0 or 1; and $R_6$ is a hydrogen atom, a monovalent aliphatic hydrocarbon, aromatic hydrocarbon or aromatic heterocyclic group, any of which may have one or more substituent thereon, a halogen atom, or a cyano, isocyano, thiocyanate, isothiocyanate, nitro, hydroxyl, mercapto, amino or amide group.

The novel amino group-containing heterocyclic derivative of the invention is an amino group-containing compound having a specific partial structure. Specifically, it is a terminal amino group-containing compound of general formula (1) below.

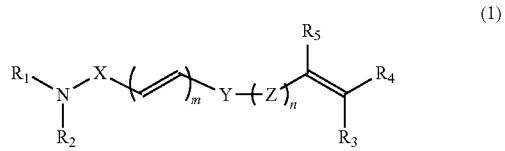

(1)

In above general formula (1), $R_1$, $R_2$, $R_4$ and $R_5$ are each independently a hydrogen atom or a monovalent organic residue which may have one or more substituent thereon. Here, $R_1$ and $R_2$ may together form a ring. Alternatively, $R_1$ and/or $R_2$ may form a ring together with X. $R_3$ is an anchoring group which is capable of attaching to an inorganic porous material having semiconductor characteristics. X is a divalent aromatic hydrocarbon group or a combination of two or more divalent aromatic hydrocarbon groups, which divalent aromatic hydrocarbon group may have one or more substituent and may be condensed from two or more rings. The letter m is an integer from 1 to 3, and the letter n is an integer from 0 to 3. Y is a divalent aromatic heterocyclic group having a sulfur atom, which divalent aromatic heterocyclic group may have one or more substituent and may be condensed from two or more rings. Z is a divalent aromatic heterocyclic group, a divalent aromatic hydrocarbon group, a divalent unsaturated hydrocarbon group or a combination thereof. The divalent aromatic heterocyclic group, divalent aromatic hydrocarbon group and divalent unsaturated hydrocarbon group may have one or more substituent. The divalent aromatic heterocyclic group and divalent aromatic hydrocarbon group may be condensed from two or more rings. The structure from X to the anchoring group $R_3$ forms a π-conjugated system. The double bonds in formula (1) may allow the formation of any cis-trans isomer configuration.

First, X in general formula (1) is described. X represents a divalent aromatic hydrocarbon group or a combination of two or more divalent aromatic hydrocarbon groups. The divalent aromatic hydrocarbon group may have one or more substituent and may be condensed from two or more rings. In cases where the divalent aromatic hydrocarbon group has one or more substituent, two or more substituents may bond together to form a ring. Alternatively, $R_1$ and/or $R_2$ may form a ring together with X. As used herein, "a combination of two or more divalent aromatic hydrocarbon groups" refers to a structure in which two or more divalent aromatic hydrocarbon groups are directly bonded together.

Examples of divalent aromatic hydrocarbon groups include phenylene, naphthylene, anthrylene and phenanthrylene groups, any of which may have one or more substituent. Examples of groups having a structure in which two or more divalent aromatic hydrocarbon groups are directly bonded together include biphenylene and terphenylene groups.

Y is a divalent aromatic heterocyclic group having a sulfur atom. The divalent aromatic heterocyclic group may have one or more substituent. Moreover, the divalent aromatic heterocyclic group may have a monocyclic structure or may have a condensed ring structure resulting from the condensation of two or more rings. Examples of such divalent aromatic heterocyclic groups include thienylene and thienothienylene groups, and preferably 2,5-thienylene and 2,5-thienothienylene groups.

Z in general formula (1) is a divalent aromatic heterocyclic group, a divalent aromatic hydrocarbon group, a divalent unsaturated hydrocarbon group or a combination thereof. The divalent aromatic heterocyclic group, the divalent aromatic hydrocarbon group and the divalent unsaturated hydrocarbon group may have one or more substituent thereon. The divalent aromatic heterocyclic group and the divalent aromatic hydrocarbon group may be condensed from two or more rings. The structure from X to the anchoring group $R_3$ forms a π-conjugated system.

Combinations of these cyclic and other groups are exemplified by structures in which two or more divalent aromatic heterocyclic groups are directly bonded together, structures in which two or more divalent aromatic hydrocarbon groups are directly bonded together, structures in which one or more divalent aromatic heterocyclic group is directly bonded to one or more divalent aromatic hydrocarbon group, structures in which two or more divalent aromatic heterocyclic groups are bonded together through a divalent unsaturated hydrocarbon group, structures in which two or more divalent aromatic hydrocarbon groups are bonded together through a divalent unsaturated hydrocarbon group, and structures in which one or more divalent aromatic heterocyclic group and one or more divalent aromatic hydrocarbon group are bonded together through a divalent unsaturated hydrocarbon group. Those structures where groups are bonded together through a divalent unsaturated hydrocarbon group are structures in which the π electrons of the divalent aromatic heterocyclic groups and the aromatic hydrocarbon groups are conjugated with the π electrons of the divalent unsaturated hydrocarbon group therebetween.

Examples of divalent aromatic heterocyclic groups include thienylene groups and thienothienylene groups, any of which may have one or more substituent, and preferably 2,5-thienylene and 2,5-thienothienylene groups.

Examples of the divalent aromatic hydrocarbon groups include phenylene, naphthylene, anthrylene and phenanthrylene groups, any of which may have one or more substituent. Examples of groups having a structure in which divalent aromatic hydrocarbon groups are directly bonded together include biphenylene and terphenylene groups.

Examples of divalent unsaturated hydrocarbon groups include conjugated acyclic linkages such as —CH═CH—, —CH═CH—CH═CH—, —CH═CH—CH═CH—CH═CH— and —CH═CH—C═C—; cyclic linkages having one or more unsaturated bond such as 1-cyclohexen-1,2-ylene and 1-cyclopenten-1,2-ylene; and structures which are combinations of the above acyclic linkages and cyclic linkages.

The terminal amino group-containing heterocyclic derivative of the invention represented by general formula (1) is suitable as a sensitizing dye for photovoltaic conversion in dye-sensitized photovoltaic cells.

The solar radiation which reaches the Earth is scattered or absorbed by the upper atmosphere surrounding the Earth, resulting in a spectral distribution of from about 300 to about 3,000 nm. In a dye-sensitized photovoltaic cell, owing to the influence of, for example, the semiconductor electrode potential and the redox potential of the electrolyte, a range of from 300 to 1200 nm is thought to be effective as the absorption wavelength region in which sunlight can be converted to electrical energy. Moreover, sunlight has a high irradiance primarily in the visible region, with the energy in the visible region of 400 to 800 nm accounting for 55% of the overall energy of sunlight.

Therefore, the energy of sunlight can be efficiently utilized by employing dyes having a broad absorption band in the visible region as the sensitizing dyes for photovoltaic conversion in dye-sensitized photovoltaic cells.

The dyes employed as the sensitizing dyes for photovoltaic conversion in dye-sensitized photovoltaic cells preferably have a broader absorption band in the near-ultraviolet/visible/near infrared region, and most preferably have a broad absorption band in the visible region. Hence, it is preferable for such dyes, along with having the broad absorption in the visible region determined by measurement of the absorption spectrum, to have absorption edge and absorption maximum wavelengths on the longer wavelength side. To make efficient use of sunlight, it is preferable for the molar absorption coefficient at the absorption maximum wavelength to be large. While the above condition can be satisfied by extension of the conjugated system with double bonds, from the standpoint of dye synthesis, this tends to result in a multistep synthesis process, possibly lowering the yield and increasing the costs of reagents and the like. Moreover, in terms of durability, the presence of oxygen and the like may drastically lower the stability to light in particular.

Compounds such as those of general formula (1) in which a thienylene group or a thienothienylene group has been introduced as part of the conjugated system provide one approach for designing dye structures which satisfy these conditions.

In addition, the energy levels of the dye known as the highest occupied molecular orbital (HOMO) and the lowest unoccupied molecular orbital (LUMO) play a large role in the performance of a dye-sensitized solar cell. It is required that the HOMO energy level (one-electron oxidation potential) for the dye be a lower energy band than the redox potential of the electron transport agent in the electrolyte, and that the LUMO energy level (one-electron oxidation potential) for the dye be a higher energy band than the semiconductor conduction. Because the balance between the dye and the individual components of the photovoltaic cell which affect the dye is important for the optimum energy level, a suitable energy difference between each individual component and the dye is believed to be necessary (see Ashraful Islam, Hideki Sugihara and Hidenori Arakawa Molecular design of ruthenium (II) polypyridyl photosensitizers for efficient nanocrystalline $TiO_2$ solar cell," Journal of Photochemistry and Photobiology A: Chemistry).

Basically, energy levels such as HOMO and LUMO are largely dependent on the molecular skeleton. Tuning the energy level to the optimal position involves modifying the skeleton or extending or shortening the π-conjugated system. It is known that generally, when the π-conjugated system is lengthened, the HOMO energy level rises and the LUMO energy level falls. However, there are limits to the degree to which the HOMO and LUMO energy levels of a dye can be tuned to the optimal positions by merely increasing or decreasing the length of the conjugated system.

One method that has been proposed for designing the structure of a dye which satisfies these conditions involves introducing a suitable number of fluorine atoms to suitable positions on the compound of general formula (1). Energy levels such as HOMO and LUMO can be tuned in this way. These compounds are preferably sensitizing dyes for dye-sensitized photovoltaic cells.

X in general formula (1) is preferably an aromatic hydrocarbon group which may have one or more substituent. Aromatic hydrocarbon groups such as phenylene, naphthylene or anthrylene groups which enable conjugation from the terminal amino group to the anchoring group are preferred. A 1,4-phenylene group is especially preferred. A fluorine-substituted 1,4-phenylene group is especially preferred as X. The reasons why such groups are preferred as the X moiety include the ease of introducing the amino groups required for absorption by the dye up to a longer wavelength region within the ultraviolet/visible absorption spectrum, and the ready availability of the starting materials for synthesis. Moreover, introducing fluorine atoms onto the aromatic hydrocarbon group serving as the X moiety has the effect of lowering the HOMO and LUMO energy levels of the dye. Indeed, the HOMO and LUMO energy levels can be tuned by suitably selecting the fluorine atom substitution positions and the number of such substitutions. The HOMO and LUMO energy levels can be easily measured by cyclic voltammetry (CV), which is one type of electrochemical measurement method. The HOMO energy level corresponds substantially with the one-electron oxidation potential, and the LUMO energy level corresponds substantially with the one-electron reduction potential. With regard to the aromatic hydrocarbon group X, the one-electron oxidation potential of a dye having fluorine atoms on X will shift more to the oxidation side than that of a dye having no fluorine atom on X. Similarly, the one-electron reduction potential of a dye having fluorine atoms on X will shift farther to the oxidation side than that of a dye having no fluorine atoms.

Y in general formula (1) is preferably a thienylene group or a thienothienylene group, and more preferably a 2,5-thienylene group or a 2,5-thienothienylene group. These groups may have one or more substituent. Such groups are preferred as the Y moiety because the 2- and 5-positions on the thiophene ring or the thienothiophene ring have a high activity, making synthesis easy. Moreover, attachment to the positions of π electron conjugation is easy, and the resulting compounds have been confirmed to have a broad absorption band within a visible region of the ultraviolet/visible absorption spectrum.

Moreover, in contrast with cases in which an aromatic hydrocarbon group is placed at the Y position, the absorption maximum in the visible region shifts toward the long wavelength side, which is believed to enable more effective utilization for photovoltaic energy.

Z in general formula (1) is preferably a cyclic group such as a phenylene, thienylene or thienothienylene group which may have one or more substituent thereon, or a structure like that described below which is obtained by combining cyclic groups with an acyclic linkage. In the structures shown below, the side that bonds to the Y moiety is labeled as Y. Also, (Fn) signifies that one or more fluorine atom may be substituted thereon. Any of the cyclic groups may have one or more substituent thereon, preferred examples of which include a hydrogen atom and a fluorine atom. These groups are preferable as the Z moiety because the absorption region can be easily broadened and the absorption maximum can be easily tuned, in addition to which the starting materials are readily available and synthesis is easy.

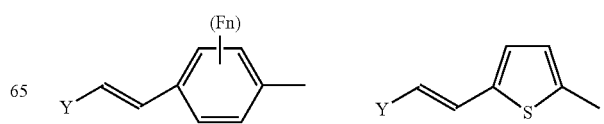

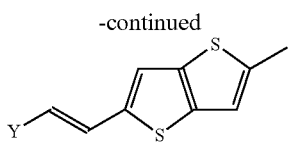

Next, $R_1$, $R_2$, $R_4$ and $R_5$ in general formula (1) are described.

$R_1$, $R_2$, $R_4$ and $R_5$ are each independently a hydrogen atom or a monovalent organic residue which may have one or more substituent thereon. $R_1$ and $R_2$ may together form a ring. Alternatively, $R_1$ and/or $R_2$ may form a ring together with X.

Specific examples of the monovalent organic residues represented by $R_1$, $R_2$, $R_4$ and $R_5$ include aliphatic hydrocarbon groups, aromatic hydrocarbon groups and aromatic heterocyclic group, any of which may have one or more substituent; halogen atoms; cyano, isocyano, thiocyanate, isothiocyanate, nitro, hydroxyl, mercapto, amino and amide groups; and groups of general formula (2) below.

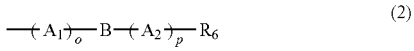

(2)

In above general formula (2), $A_1$ and $A_2$ are each independently O, NH or S; B is carbonyl, thiocarbonyl, sulfinyl or sulfonyl; the letters o and p are each independently 0 or 1; and $R_6$ is a hydrogen atom, a monovalent aliphatic hydrocarbon, aromatic hydrocarbon or aromatic heterocyclic group, any of which may have one or more substituent thereon, a halogen atom, or a cyano, isocyano, thiocyanate, isothiocyanate, nitro, hydroxyl, mercapto, amino or amide group.

As used herein, "monovalent aliphatic hydrocarbon group" refers to a monovalent aliphatic hydrocarbon group of 1 to 40 carbons which may have a linear structure, a branched structure or a cyclic structure, and which may have unsaturated bonds. Moreover, the monovalent aliphatic hydrocarbon group may have one or more substituent, and one or more carbon atoms in this monovalent aliphatic hydrocarbon group may be substituted with an oxygen, sulfur or nitrogen atom. Exemplary monovalent aliphatic hydrocarbon groups include alkyl, alkenyl, alkynyl, cycloalkyl and alkoxy groups of from 1 to 30 carbons.

Specific examples of monovalent aliphatic hydrocarbon groups include $C_{1-8}$ alkyl groups such as methyl, ethyl, n-propyl, isopropyl, n-butyl, isobutyl, sec-butyl, tert-butyl, 1-pentyl, 1-hexyl, 1-heptyl, 1-octyl and 2-ethyl-1-hexyl; $C_{2-4}$ alkenyl groups such as 1-propenyl, isopropenyl, 2-propenyl, allyl, 1-butenyl, 2-butenyl, 3-butenyl, 1-methyl-3-propenyl, 2-methyl-1-propenyl and 2-methyl-2-propenyl; $C_{2-4}$ alkynyl groups such as ethynyl, 1 butynyl, 2-butynyl, and 3-butynyl; $C_{3-10}$ saturated cycloalkyl groups such as cyclopropyl, cyclobutyl, cyclopentyl, cyclohexyl, cycloheptyl, cyclooctyl, cyclononyl and cyclodecyl; and $C_{3-7}$ unsaturated cycloalkyl groups such as 2-cyclopenten-1-yl and 2-cyclohexen-1-yl.

Monovalent aromatic hydrocarbon groups are exemplified by aromatic hydrocarbon groups having a monovalent monocyclic structure or a condensed ring structure, and monovalent ring assembly aromatic hydrocarbon group. Specific examples include phenyl, naphthyl, anthryl, phenanthryl, triphenyl and pyrenyl groups. Moreover, the monovalent aromatic hydrocarbon groups may bond with part of the skeleton of general formula (1) through an oxygen, sulfur or nitrogen atom. Examples of such groups include phenoxy and naphthyloxy groups.

Examples of preferred monovalent aromatic hydrocarbon groups include $C_{6-14}$ monovalent aromatic hydrocarbon groups such as phenyl, o-tolyl, m-tolyl, p-tolyl, o-anisoyl, m-anisoyl, p-anisoyl, 1-naphthyl, 2-naphthyl and 9-phenanthryl groups.

Monovalent aromatic heterocyclic groups are exemplified by aromatic heterocyclic groups having a monovalent monocyclic structure or a condensed ring structure, and by monovalent ring assembly aromatic heterocyclic groups. Specific examples include 2-furyl, 3-furyl, 2-thienyl, 3-thienyl, 2-selenyl, 3-selenyl, 1-pyrrolyl, 2-pyrrolyl, 3-pyrrolyl, 2-pyridyl, 3-pyridyl, 4-pyridyl, 2-quinolyl, 3-quinolyl, 4-quinolyl, 5-quinolyl, 6-quinolyl, 7-quinolyl, 8-quinolyl, 1-isoquinolyl, 2-quinoxalyl, 2-benzofuryl, 2-benzothienyl, 2-thienothienyl, 3-thienothienyl, 2-selenoselenyl, 3-selenoselenyl, 2-thiazoyl and 2-thiazothiazoyl groups.

Preferred examples of monovalent aromatic heterocyclic groups include $C_{4-12}$ aromatic heterocyclic groups such as 2-thienyl, 2-selenyl, 2-benzothienyl, 2-benzoselenyl, 2-thienothienyl, 2-selenoselenyl and 2-dithienyl groups.

Aliphatic hydrocarbon groups in which $R_1$ and $R_2$ together form a cyclic structure are exemplified by divalent linkage groups. Preferred examples of divalent linkage groups include $C_{4-6}$ saturated alkylene groups such as tetramethylene, pentamethylene and hexamethylene groups. For example, in the case of a pentamethylene group, the ring formed by $R_1$ and $R_2$ together with the nitrogen atom in the amine moiety of general formula (1) is a piperidine ring.

Alternatively, if the aliphatic hydrocarbon group in which $R_1$ and $R_2$ together forms a cyclic structure is a pentamethylene group and an oxygen atom is substituted for a carbon atom, the ring created by $R_1$ and $R_2$ together with the nitrogen atom in the amine moiety of general formula (1) forms, for example, a morpholine ring.

Aromatic hydrocarbon groups in which $R_1$ and $R_2$ together form a cyclic structure are exemplified by divalent linkage groups composed of an aromatic hydrocarbon group having a monocyclic structure or a condensed ring structure, and divalent linkage groups composed of a ring assembly aromatic hydrocarbon group. Specific examples of such divalent linkage groups include 2,2'-biphenylene, —Ph—S—Ph— and 4,5-phenanthrylene groups. A 2,2-biphenylene group is preferred.

Aromatic heterocyclic groups in which $R_1$ and $R_2$ together form a cyclic structure are exemplified by divalent linkage groups composed of an aromatic hydrocarbon group having a monocyclic structure or a condensed ring structure, and divalent linkage groups composed of a ring assembly aromatic heterocyclic group. A specific example of such a divalent linkage group is the 3,3'-bithienylene group.

For ease of synthesis and other reasons, $C_{1-4}$ alkyl groups and $C_{6-14}$ monovalent aromatic hydrocarbon groups are preferred as $R_1$ and $R_2$. $C_{1-4}$ alkyl groups are especially preferred.

$R_4$ and $R_5$ are each preferably a hydrogen atom, a halogen atom or a $C_{1-20}$ monovalent organic residue. It is preferable for the monovalent organic residue to be substituted. $R_4$ and $R_5$ are each most preferably a hydrogen atom or an electron-withdrawing group.

As used herein, "electron-withdrawing group" refers to a group having a Hammett substituent constant σ greater than 0, Specific examples of the electron-withdrawing groups of $R_4$ and $R_5$ include, but are not limited to, cyano, carboxyl, acyl, formyl, aryloxycarbonyl, alkyloxycarbonyl, alkylsulfonyl, arylsulfonyl, alkylsulfinyl, arylsulfinyl, nitro and perfluoroalkyl groups.

Examples of acyl groups include acetyl, propionyl, pivaroyl, acryloyl, methacryloyl, benzoyl, toluoyl and cinnamoyl groups.

Examples of aryloxycarbonyl groups include phenoxycarbonyl, naphthyloxycarbonyl and 4-fluorophenyloxycarbonyl groups.

Examples of alkylsulfonyl groups include mesyl, ethylsulfonyl, propylsulfonyl, trifluorosulfonyl and nonafluoro-t-butylsulfonyl groups.

Examples of arylsulfonyl groups include benzenesulfonyl and toluenesulfonyl groups.

Examples of alkylsulfinyl groups include methylsulfinyl, ethylsulfinyl and propylsulfinyl groups.

Examples of arylsulfinyl groups include phenylsulfinyl and toluoylsulfinyl groups.

Perfluoroalkyl groups are alkyl groups in which all the hydrogen atoms on carbon atoms have been substituted with fluorine atoms. The number of carbon atoms is preferably from 1 to 20. Perfluoroalkyl groups may have oxygen atoms and sulfur atoms introduced thereon.

Of the above, for ease of synthesis and electron-withdrawing strength, $R_4$ is preferably a cyano group. $R_5$ is preferably a hydrogen atom or a cyano group.

$R_3$ is an anchoring group which is capable of attaching to an inorganic porous material having semiconductor characteristics. Particles of an inorganic oxide having semiconductor characteristics, such as titanium oxide, tin oxide and zinc oxide, which have been rendered porous may be used as the inorganic porous material having semiconductor characteristics. Accordingly, the anchoring group broadly includes groups which are capable of attaching to such porous inorganic oxide particles. Preferred examples of such anchoring groups include carboxyl groups, phosphoric acid groups and sulfonic acid groups. Of these, carboxyl groups are especially preferred because they readily attach to porous inorganic oxide particles.

For such purposes as to increase solubility, the foregoing carboxyl, sulfonic acid and phosphoric acid groups may bond with a cation to form a salt. Examples of cations capable of forming salts include ammonium ions, alkali metal ions and alkaline earth metal ions. Ammonium ions are exemplified by tetraalkylammonium ions such as the tetramethylammonium ion. Alkali metal ions are exemplified by sodium, potassium and lithium ions. Alkaline earth metal ions are exemplified by magnesium and calcium ions.

The letter m in general formula (1) is an integer from 1 to 3. For ease of synthesis and stability of the compound, it is preferable for m to be 1.

The letter n in general formula (1) is the integer 0 or 1. If n is 0, there is no Z moiety, which means that the carbon atom bonded to $R_5$ is directly bonded to Y. For ease of synthesis, it is preferable that n be 0. For extension of the conjugated system, it is preferable that n be 1.

Specific examples of the inventive terminal amino group-containing heterocyclic derivative of general formula (1) include, but are not limited to, those shown below.

In the following examples, "Ph" represents a phenyl group, "Me" represents a methyl group, "Pr" represents an n-propyl group, and "Bu" represents an n-butyl group.

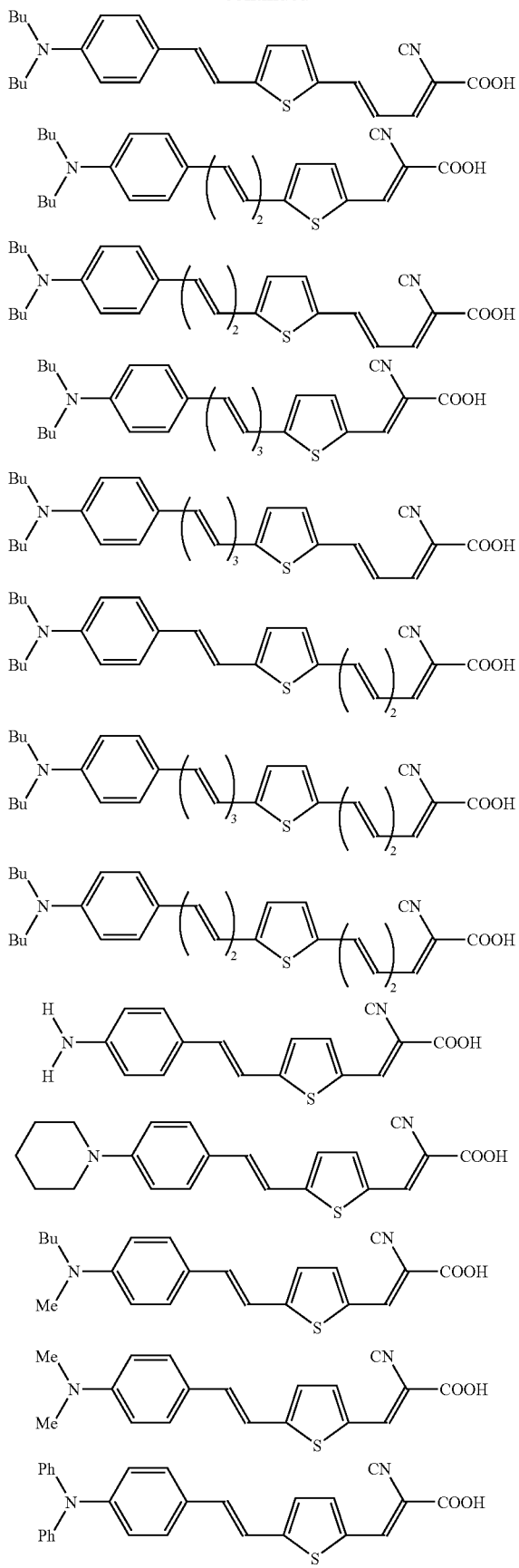

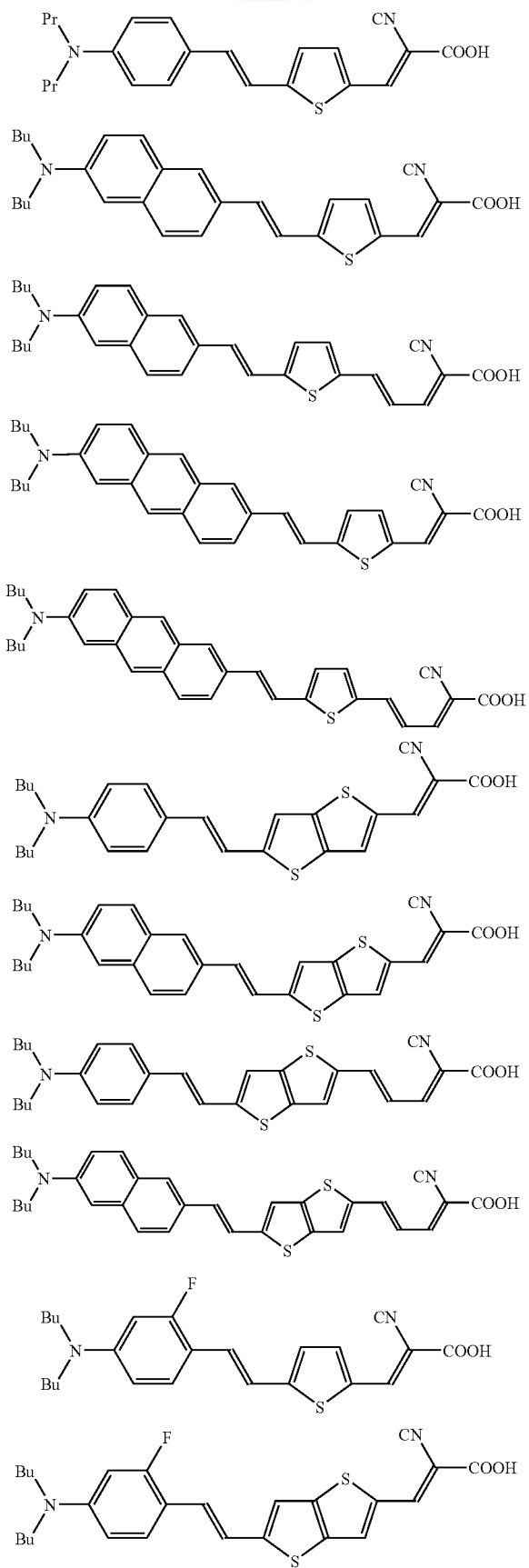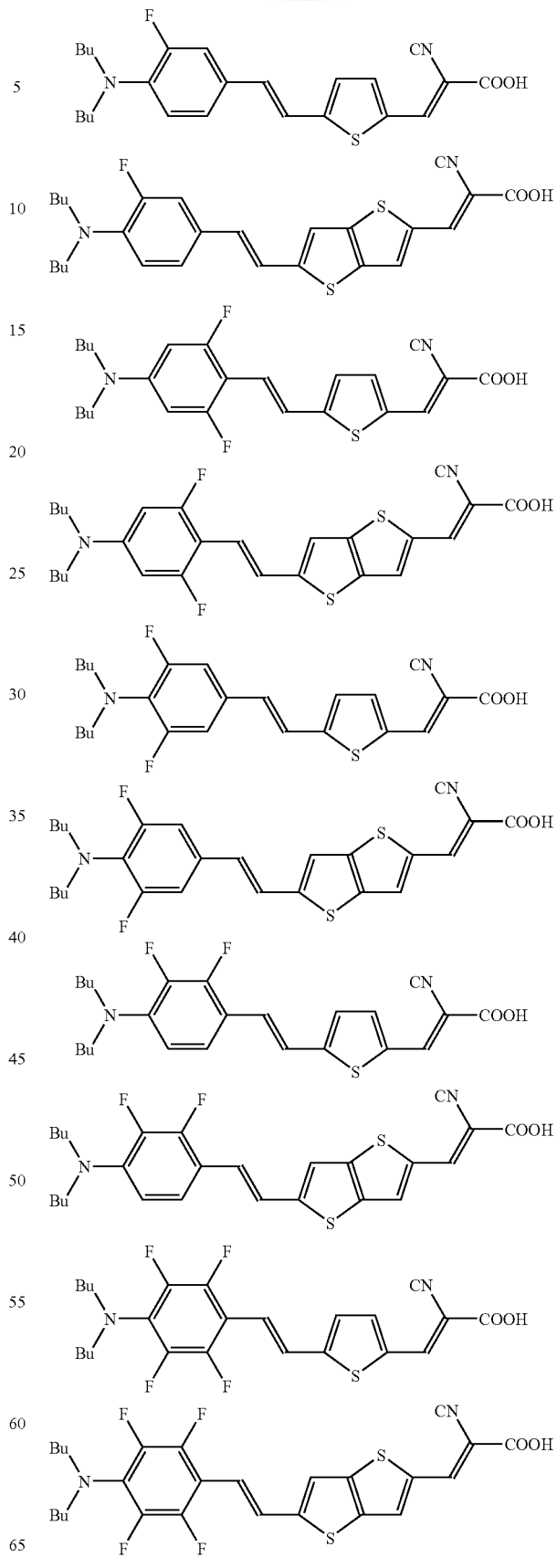

Examples of preferred structures in the present invention are shown below.

For the sake of convenience, the following abbreviations are used below for cyclic groups serving as the X, Y and Z moieties in general formula (1). The orientation of a cyclic group is the orientation when it is inserted directly as shown into general formula (1). For example, in the case of a cyclic group serving as the X moiety, the left side of the cyclic group is bonded to the nitrogen atom bonded to $R_1$ and $R_2$, and the right side of the cyclic group is bonded to a carbon atom in a group represented by $(CH=CH)_m$.

| Structure | Symbol | Structure | Symbol |
|---|---|---|---|
| (phenyl) | Ph1 | (thiophene) | Th1 |
| (F-phenyl) | Ph2 | (thienothiophene) | Th5 |
| (F-phenyl) | Ph3 | (naphthalene) | Na1 |
| (F-phenyl) | Ph4 | (F-naphthalene) | Na2 |
| (F-phenyl) | Ph5 | (F-naphthalene) | Na3 |
| (F-phenyl) | Ph6 | (F-naphthalene) | Na4 |
| (F-phenyl) | Ph7 | (F-naphthalene) | Na5 |
| (F-phenyl) | Ph8 | (F-naphthalene) | Na6 |
| (F-phenyl) | Ph9 | (F-naphthalene) | Na7 |

Also, the skeletal structures of the compounds listed in the following tables are indicated by structural formulas appearing prior to the respective tables. In these structural formulas, a cyclic group denoted by (Fn) indicates that it may be substituted with one or more fluorine atom, and a cyclic group denoted by Fn indicates that it is substituted with one or more fluorine atom.

TABLE 1

| No. | $R_1$ | $R_2$ | X | m | Y | Z | n | $R_3$ | $R_4$ | $R_5$ |
|---|---|---|---|---|---|---|---|---|---|---|
| 1 | $CH_3$ | $C_2H_5$ | Ph1 | 1 | Th1 | — | 0 | COOH | CN | H |
| 2 | $C_2H_5$ | $C_2H_5$ | Ph1 | 1 | Th1 | — | 0 | COOH | CN | H |
| 3 | $n\text{-}C_3H_7$ | $n\text{-}C_4H_9$ | Ph1 | 1 | Th1 | — | 0 | COOH | CN | H |
| 4 | $CH_3$ | Ph1 | Ph1 | 1 | Th1 | — | 0 | COOH | CN | H |

TABLE 2

| No. | $R_1$ | $R_2$ | X | m | Y | Z | n | $R_3$ | $R_4$ | $R_5$ |
|---|---|---|---|---|---|---|---|---|---|---|
| 5 | $CH_3$ | $CH_3$ | Na1 | 1 | Th1 | — | 0 | COOH | CN | H |
| 6 | $n\text{-}C_4H_9$ | $n\text{-}C_4H_9$ | Na2 | 1 | Th1 | — | 0 | COOH | CN | H |
| 7 | $n\text{-}C_4H_9$ | $n\text{-}C_4H_9$ | Na3 | 1 | Th1 | — | 0 | COOH | CN | H |
| 8 | $n\text{-}C_4H_9$ | $n\text{-}C_4H_9$ | Na4 | 1 | Th1 | — | 0 | COOH | CN | H |
| 9 | $n\text{-}C_4H_9$ | $n\text{-}C_4H_9$ | Na5 | 1 | Th1 | — | 0 | COOH | CN | H |
| 10 | $n\text{-}C_4H_9$ | $n\text{-}C_4H_9$ | Na6 | 1 | Th1 | — | 0 | COOH | CN | H |
| 11 | $n\text{-}C_4H_9$ | $n\text{-}C_4H_9$ | Na7 | 1 | Th1 | — | 0 | COOH | CN | H |

TABLE 3

| No. | $R_1$ | $R_2$ | X | m | Y | Z | n | $R_3$ | $R_4$ | $R_5$ |
|---|---|---|---|---|---|---|---|---|---|---|
| 12 | $n\text{-}C_4H_9$ | $n\text{-}C_4H_9$ | Ph7 | 1 | Th1 | — | 0 | COOH | CN | H |
| 13 | $n\text{-}C_4H_9$ | $n\text{-}C_4H_9$ | Ph8 | 1 | Th1 | — | 0 | COOH | CN | H |

TABLE 3-continued

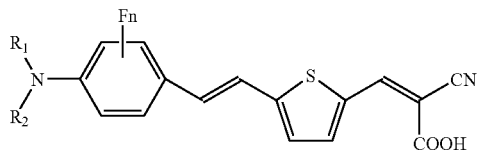

| No. | R₁ | R₂ | X | m | Y | Z | n | R₃ | R₄ | R₅ |
|-----|------|------|-----|---|-----|---|---|------|-----|----|
| 14 | CH₃ | CH₃ | Ph2 | 1 | Th1 | — | 0 | COOH | CN | H |
| 15 | C₂H₅ | CH₃ | Ph2 | 1 | Th1 | — | 0 | COOH | CN | H |
| 16 | Ph1 | Ph1 | Ph2 | 1 | Th1 | — | 0 | COOH | CN | H |
| 17 | CH₃ | CH₃ | Ph4 | 1 | Th1 | — | 0 | COOH | CN | H |
| 18 | C₂H₅ | CH₃ | Ph4 | 1 | Th1 | — | 0 | COOH | CN | H |
| 19 | Ph1 | Ph1 | Ph4 | 1 | Th1 | — | 0 | COOH | CN | H |

TABLE 4

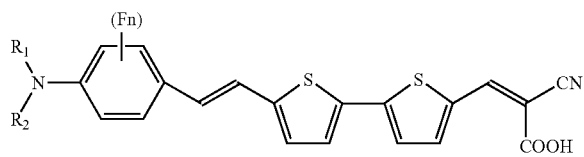

| No. | R₁ | R₂ | X | m | Y | Z | n | R₃ | R₄ | R₅ |
|-----|------|------|-----|---|-----|-----|---|------|-----|----|
| 20 | n-C₄H₉ | n-C₄H₉ | Ph1 | 1 | Th1 | Th1 | 1 | COOH | CN | H |
| 21 | n-C₄H₉ | n-C₄H₉ | Ph2 | 1 | Th1 | Th1 | 1 | COOH | CN | H |
| 22 | n-C₄H₉ | n-C₄H₉ | Ph3 | 1 | Th1 | Th1 | 1 | COOH | CN | H |
| 23 | n-C₄H₉ | n-C₄H₉ | Ph4 | 1 | Th1 | Th1 | 1 | COOH | CN | H |
| 24 | n-C₄H₉ | n-C₄H₉ | Ph5 | 1 | Th1 | Th1 | 1 | COOH | CN | H |
| 25 | n-C₄H₉ | n-C₄H₉ | Ph6 | 1 | Th1 | Th1 | 1 | COOH | CN | H |
| 26 | n-C₄H₉ | n-C₄H₉ | Ph7 | 1 | Th1 | Th1 | 1 | COOH | CN | H |
| 27 | n-C₄H₉ | n-C₄H₉ | Ph8 | 1 | Th1 | Th1 | 1 | COOH | CN | H |
| 28 | n-C₄H₉ | n-C₄H₉ | Ph9 | 1 | Th1 | Th1 | 1 | COOH | CN | H |

TABLE 5

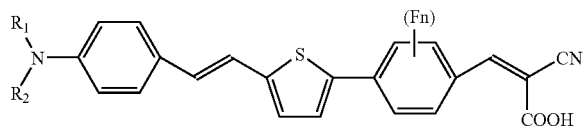

| No. | R₁ | R₂ | X | m | Y | Z | n | R₃ | R₄ | R₅ |
|-----|------|------|-----|---|-----|-----|---|------|-----|----|
| 29 | n-C₄H₉ | n-C₄H₉ | Ph1 | 1 | Th1 | Ph1 | 1 | COOH | CN | H |
| 30 | n-C₄H₉ | n-C₄H₉ | Ph1 | 1 | Th1 | Ph2 | 1 | COOH | CN | H |
| 31 | n-C₄H₉ | n-C₄H₉ | Ph1 | 1 | Th1 | Ph3 | 1 | COOH | CN | H |
| 32 | n-C₄H₉ | n-C₄H₉ | Ph1 | 1 | Th1 | Ph4 | 1 | COOH | CN | H |
| 33 | n-C₄H₉ | n-C₄H₉ | Ph1 | 1 | Th1 | Ph5 | 1 | COOH | CN | H |
| 34 | n-C₄H₉ | n-C₄H₉ | Ph1 | 1 | Th1 | Ph6 | 1 | COOH | CN | H |
| 35 | n-C₄H₉ | n-C₄H₉ | Ph1 | 1 | Th1 | Ph7 | 1 | COOH | CN | H |
| 36 | n-C₄H₉ | n-C₄H₉ | Ph1 | 1 | Th1 | Ph8 | 1 | COOH | CN | H |

TABLE 5-continued

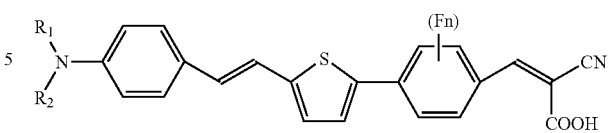

| No. | R₁ | R₂ | X | m | Y | Z | n | R₃ | R₄ | R₅ |
|-----|------|------|-----|---|-----|-----|---|------|-----|----|
| 37 | n-C₄H₉ | n-C₄H₉ | Ph1 | 1 | Th1 | Ph9 | 1 | COOH | CN | H |

TABLE 6

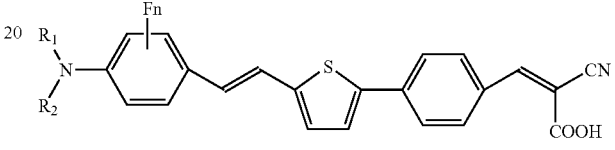

| No. | R₁ | R₂ | X | m | Y | Z | n | R₃ | R₄ | R₅ |
|-----|------|------|-----|---|-----|-----|---|------|-----|----|
| 38 | n-C₄H₉ | n-C₄H₉ | Ph2 | 1 | Th1 | Ph1 | 1 | COOH | CN | H |
| 39 | n-C₄H₉ | n-C₄H₉ | Ph3 | 1 | Th1 | Ph1 | 1 | COOH | CN | H |
| 40 | n-C₄H₉ | n-C₄H₉ | Ph4 | 1 | Th1 | Ph1 | 1 | COOH | CN | H |
| 41 | n-C₄H₉ | n-C₄H₉ | Ph5 | 1 | Th1 | Ph1 | 1 | COOH | CN | H |
| 42 | n-C₄H₉ | n-C₄H₉ | Ph6 | 1 | Th1 | Ph1 | 1 | COOH | CN | H |
| 43 | n-C₄H₉ | n-C₄H₉ | Ph7 | 1 | Th1 | Ph1 | 1 | COOH | CN | H |
| 44 | n-C₄H₉ | n-C₄H₉ | Ph8 | 1 | Th1 | Ph1 | 1 | COOH | CN | H |
| 45 | n-C₄H₉ | n-C₄H₉ | Ph9 | 1 | Th1 | Ph1 | 1 | COOH | CN | H |

TABLE 7

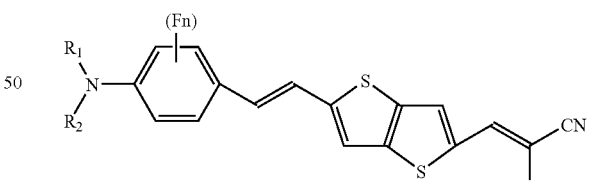

| No. | R₁ | R₂ | X | m | Y | Z | n | R₃ | R₄ | R₅ |
|-----|------|------|-----|---|-----|---|---|------|-----|----|
| 46 | n-C₄H₉ | n-C₄H₉ | Ph7 | 1 | Th5 | — | 0 | COOH | CN | H |
| 47 | n-C₄H₉ | n-C₄H₉ | Ph8 | 1 | Th5 | — | 0 | COOH | CN | H |
| 48 | CH₃ | CH₃ | Ph1 | 1 | Th5 | — | 0 | COOH | CN | H |
| 49 | C₂H₅ | CH₃ | Ph1 | 1 | Th5 | — | 0 | COOH | CN | H |
| 50 | Ph1 | Ph1 | Ph1 | 1 | Th5 | — | 0 | COOH | CN | H |
| 51 | CH₃ | CH₃ | Ph2 | 1 | Th5 | — | 0 | COOH | CN | H |
| 52 | C₂H₅ | CH₃ | Ph2 | 1 | Th5 | — | 0 | COOH | CN | H |
| 53 | Ph1 | Ph1 | Ph2 | 1 | Th5 | — | 0 | COOH | CN | H |
| 54 | CH₃ | CH₃ | Ph4 | 1 | Th5 | — | 0 | COOH | CN | H |
| 55 | C₂H₅ | CH₃ | Ph4 | 1 | Th5 | — | 0 | COOH | CN | H |
| 56 | Ph1 | Ph1 | Ph4 | 1 | Th5 | — | 0 | COOH | CN | H |

TABLE 8

| No. | $R_1$ | $R_2$ | X | m | Y | Z | n | $R_3$ | $R_4$ | $R_5$ |
|---|---|---|---|---|---|---|---|---|---|---|
| 57 | n-$C_4H_9$ | n-$C_4H_9$ | Ph1 | 1 | Th1 | CH=CH-Th1 | 1 | COOH | CN | H |
| 58 | n-$C_4H_9$ | n-$C_4H_9$ | Ph2 | 1 | Th1 | CH=CH-Th1 | 1 | COOH | CN | H |
| 59 | n-$C_4H_9$ | n-$C_4H_9$ | Ph3 | 1 | Th1 | CH=CH-Th1 | 1 | COOH | CN | H |
| 60 | n-$C_4H_9$ | n-$C_4H_9$ | Ph4 | 1 | Th1 | CH=CH-Th1 | 1 | COOH | CN | H |
| 61 | n-$C_4H_9$ | n-$C_4H_9$ | Ph5 | 1 | Th1 | CH=CH-Th1 | 1 | COOH | CN | H |
| 62 | n-$C_4H_9$ | n-$C_4H_9$ | Ph6 | 1 | Th1 | CH=CH-Th1 | 1 | COOH | CN | H |
| 63 | n-$C_4H_9$ | n-$C_4H_9$ | Ph7 | 1 | Th1 | CH=CH-Th1 | 1 | COOH | CN | H |
| 64 | n-$C_4H_9$ | n-$C_4H_9$ | Ph8 | 1 | Th1 | CH=CH-Th1 | 1 | COOH | CN | H |
| 65 | n-$C_4H_9$ | n-$C_4H_9$ | Ph9 | 1 | Th1 | CH=CH-Th1 | 1 | COOH | CN | H |

TABLE 9

| No. | $R_1$ | $R_2$ | X | m | Y | Z | n | $R_3$ | $R_4$ | $R_5$ |
|---|---|---|---|---|---|---|---|---|---|---|
| 66 | n-$C_4H_9$ | $C_4H_9$ | Ph1 | 1 | Th1 | CH=CH-Ph1 | 1 | COOH | CN | H |
| 67 | n-$C_4H_9$ | $C_4H_9$ | Ph1 | 1 | Th1 | CH=CH-Ph2 | 1 | COOH | CN | H |
| 68 | n-$C_4H_9$ | $C_4H_9$ | Ph1 | 1 | Th1 | CH=CH-Ph3 | 1 | COOH | CN | H |
| 69 | n-$C_4H_9$ | $C_4H_9$ | Ph1 | 1 | Th1 | CH=CH-Ph4 | 1 | COOH | CN | H |
| 70 | n-$C_4H_9$ | $C_4H_9$ | Ph1 | 1 | Th1 | CH=CH-Ph5 | 1 | COOH | CN | H |
| 71 | n-$C_4H_9$ | $C_4H_9$ | Ph1 | 1 | Th1 | CH=CH-Ph6 | 1 | COOH | CN | H |
| 72 | n-$C_4H_9$ | $C_4H_9$ | Ph1 | 1 | Th1 | CH=CH-Ph7 | 1 | COOH | CN | H |
| 73 | n-$C_4H_9$ | $C_4H_9$ | Ph1 | 1 | Th1 | CH=CH-Ph8 | 1 | COOH | CN | H |
| 74 | n-$C_4H_9$ | $C_4H_9$ | Ph1 | 1 | Th1 | CH=CH-Ph9 | 1 | COOH | CN | H |

TABLE 10

| No. | $R_1$ | $R_2$ | X | m | Y | Z | n | $R_3$ | $R_4$ | $R_5$ |
|---|---|---|---|---|---|---|---|---|---|---|
| 75 | n-$C_4H_9$ | n-$C_4H_9$ | Ph2 | 1 | Th1 | CH=CH-Ph1 | 1 | COOH | CN | H |
| 76 | n-$C_4H_9$ | n-$C_4H_9$ | Ph3 | 1 | Th1 | CH=CH-Ph1 | 1 | COOH | CN | H |
| 77 | n-$C_4H_9$ | n-$C_4H_9$ | Ph4 | 1 | Th1 | CH=CH-Ph1 | 1 | COOH | CN | H |
| 78 | n-$C_4H_9$ | n-$C_4H_9$ | Ph5 | 1 | Th1 | CH=CH-Ph1 | 1 | COOH | CN | H |
| 79 | n-$C_4H_9$ | n-$C_4H_9$ | Ph6 | 1 | Th1 | CH=CH-Ph1 | 1 | COOH | CN | H |
| 80 | n-$C_4H_9$ | n-$C_4H_9$ | Ph7 | 1 | Th1 | CH=CH-Ph1 | 1 | COOH | CN | H |
| 81 | n-$C_4H_9$ | n-$C_4H_9$ | Ph8 | 1 | Th1 | CH=CH-Ph1 | 1 | COOH | CN | H |
| 82 | n-$C_4H_9$ | n-$C_4H_9$ | Ph9 | 1 | Th1 | CH=CH-Ph1 | 1 | COOH | CN | H |

The sensitizing dye for photovoltaic conversion of the invention is characterized by including the above-described terminal amino group-containing heterocyclic derivative of general formula (1). The inventive sensitizing dye for photovoltaic conversion may further include another photosensitizing dye so as to absorb sunlight in spectral regions not fully covered by the terminal amino group-containing heterocyclic derivative of general formula (1). Examples of other sensitizing dyes which may be used for such a purpose include cyanine dyes, melocyanine dyes, mercurochrome dyes, xanthene dyes, porphyrin dyes, phthalocyanine dyes, azo dyes and coumarin dyes. Metal complex dyes such as ruthenium complex dyes may also be used as the other sensitizing dye in the invention.

The photovoltaic material of the invention is formed by attaching the above-described sensitizing dye for photovoltaic conversion to an inorganic porous material having semiconductor characteristics via the anchoring group. Examples of the inorganic porous material used to form the photovoltaic material include titanium oxide, tin oxide, zinc oxide, niobium oxide, indium oxide, tungsten oxide and tantalum oxide. These may be used as combinations of two or more inorganic compounds. Of these, titanium oxide and tin oxide are preferred, and titanium oxide is especially preferred.

The photovoltaic electrode of the invention is obtained by forming a layer of the inventive photovoltaic material obtained as indicated above on a transparent electrode. The transparent electrode may be obtained by, for example, forming a clear, electrically conductive film on a transparent substrate. The transparent substrate is exemplified by glass substrates and plastic substrates. Examples of glass substrates include substrates made of silica glass, soda lime glass, borosilicate glass and lead glass. Examples of plastic substrates include substrates made of polyethylene terephthalate or polyethylene naphthalate.

The method used to form an electrically conductive film on a surface of the transparent substrate may be, for example, a method in which a film of metal oxide composed of indium oxide and tin oxide (ITO) or the like is formed such as by vapor deposition on the substrate surface, or a method in which the film is created by doping tin oxide with fluorine.

The photovoltaic electrode of the invention is created by forming a layer of the inventive photovoltaic material obtained as described above onto a transparent electrode. The method of forming a layer of the inventive photovoltaic material on a transparent electrode is exemplified by a method in which a layer of an inorganic porous material is formed on a transparent electrode, then a sensitizing dye is adsorbed onto the layer. In one example of a method of forming a layer of an inorganic porous material on a transparent electrode, an inorganic porous material is dispersed in a suitable solvent or polymer, with the further addition of suitable additives, and thereby rendered into the form of a paste which is then applied onto a transparent electrode and subsequently dried or baked. It is also possible to use a commercially available product as the inorganic porous material paste. Examples of the dispersing solvent include water, alcohol-type solvents, amine-type solvents, ketone-type solvents and hydrocarbon-type solvents. Exemplary methods of application include spin coating, screen printing, dipping and methods involving the use of a squeegee. The lower limit in the temperature at which the slurry-coated substrate is dried or baked is a temperature at which the solvent can be removed. The upper limit is a temperature at which undesirable effects such as melting of the substrate do not occur. Drying or baking is preferably carried out at a temperature which enables adhesion between the inorganic porous material and the transparent electrode to be improved.

An example of a method that may be used for adsorption of the sensitizing dye involves dissolving or dispersing the sensitizing dye in a suitable solvent, then immersing within the resulting solution or dispersion the electrode substrate on which the above-described inorganic porous material layer has been formed. Examples of the solvent for dissolving or dispersing the sensitizing dye include water, alcohol-type solvents, amine-type solvents, ketone-type solvents and hydrocarbon-type solvents. An alcohol is preferred, and ethanol is especially preferred.

The photovoltaic cell of the invention is formed by combining the above-described photovoltaic electrode with an electrically conductive counterelectrode through an electrolyte layer.

The electrolyte layer used in the photovoltaic cell is preferably composed of an electrolyte, a medium and additives. These constituents are described below. For example, the electrolyte may be a liquid electrolyte obtained by adding a redox couple to a solvent, a polymer gel electrolyte, or a solid electrolyte. Examples of the solvent used in the liquid electrolyte include nitrile solvents, carbonate solvents, glycol solvents and water. Acetonitrile and methoxyacetonitrile are especially preferred. Examples of redox couples include halogen redox couples. An iodine redox couple is especially preferred. An iodine redox couple can be obtained from a combination of iodine and an iodide ion. Examples of starting materials for the iodide ion include metal iodides and quaternary ammonium salts. Lithium iodide is especially preferred. Redox couples can be similarly obtained for bromine and other halogen compounds as well.

Examples of electrically conductive counterelectrodes include metal electrodes obtained by the vapor deposition of a metal such as platinum, rhodium, ruthenium or indium, carbon electrodes, electrically conductive polymer electrodes, and composite electrodes thereof.

Electrode assembly involves arranging the transparent electrode and the counterelectrode on either side of the layer of photovoltaic material, with spacers between the electrodes, and filling the gap between the electrodes with an electrolyte. The periphery of the photovoltaic cell may be sealed to prevent problems such as the leakage of electrolyte solution. Suitable sealants include polymer-based adhesives.

It is also possible to use one or more compound called a "coadsorbent" together with the sensitizing dye for photovoltaic conversion of the invention. The coadsorbent is adsorbed together with the sensitizing dye onto the inorganic porous material, thereby increasing the photovoltaic conversion efficiency.

As already noted above, the sensitizing dye for photovoltaic conversion of the invention is attached to an inorganic porous material having semiconductor characteristics via anchoring groups. The term "attachment" as used here is substantially synonymous with "adsorption" in the foregoing context.

Illustrative examples of coadsorbents include steroid compounds having a carboxyl group or a sulfonic acid group, and especially cholic acid derivatives (cholic acid, deoxycholic acid, chenodeoxycholic acid, taurochenodeoxycholic acid, lithocholic acid, ursodeoxycholic acid, dehydrocholic acid) and metal salts thereof, amines (e.g., pyridine, 4-t-butylpyridine, polyvinyl pyridine), and quaternary ammonium salts (e.g., tetrabutylammonium iodide, tetrahexylammonium iodide).

Examples of methods for using the above-described coadsorbent include addition after the dye has been adsorbed (attached) to the inorganic porous material, and addition to the electrolyte layer. However, suitable methods are not limited to these, so long as the coadsorbent is adsorbed (attached) to the inorganic porous material together with the sensitizing dye.

EXAMPLES

The invention is illustrated more fully below by way of examples. However, the examples provided here are not intended to limit the scope of the invention.

Example 1

Synthesis of Compound A (See Formula Below)

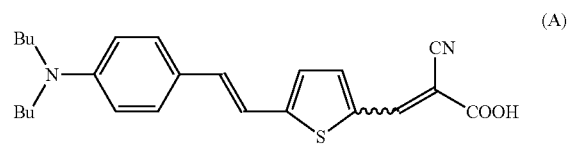

Synthesis of Compound A-1

A 500 mL four-neck flask fitted with a condenser, a thermometer, a magnetic stirrer and a dropping funnel was charged with 56 g of dibromohydantoin and 200 mL of methylene chloride. Next, 20 g of 2-methylthiophene (Wako Pure Chemical Industries, Ltd.) and 20 mL of methylene chloride were gradually added to the dropping funnel. After the completion of dropwise addition from the funnel, stirring was continued for one hour, then 1 g of the azo-type polymerization initiator V-65 (Wako Pure Chemical Industries) was added and the mixture was subsequently refluxed for 3 hours. After cooling, the white, suspended substance was removed by filtration and the filtrate was rinsed with water. The filtrate was then dried, thereby removing the solvent and yielding 21 g of product. $^1$H-NMR measurement confirmed the product to be compound A-1 (see formula below).

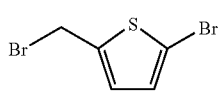

(A-1)

$^1$H-NMR (CDCl$_3$; TMS) δ 4.63 (s, —CH$_2$—Br, 2H), 6.8-7.0 (m, thiophene, 2H).

Synthesis of Compound A-2

A 500 mL four-neck flask fitted with a condenser, a thermometer and a magnetic stirrer was charged with 25.5 g of Compound A-1 obtained as described above, 16.5 g of triethyl phosphite (Kanto Chemical Co., Inc.) and 200 mL of acetonitrile, following which the mixture was heat refluxed for 3 hours under a stream of nitrogen. After cooling, the solvent and other ingredients were distilled off, yielding 29 g of product. $^1$H-NMR measurement confirmed the product to be compound A-2 (see formula below). In the formula below, "Et" represents an ethyl group.

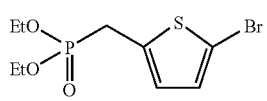

(A-2)

$^1$H-NMR (300 MHz, CDCl$_3$; TMS) δ 1.30 (t, J=7.2 Hz, —CH$_3$, 3H), 3.31 (d, J=16.2 Hz, Ar—CH$_2$—P(=O)<, 2H), 4.09 (m, —O—CH$_2$-Me, 2H), 6.65-6.80 (t, J=3.6 Hz, thiophene ring hydrogen, 1H), 6.90 (d, J=3.9 Hz, thiophene ring hydrogen, 1H).

Synthesis of Compound A-3

A 500 mL four-neck flask fitted with a condenser, a thermometer, a magnetic stirrer and a dropping funnel was charged with 14.2 g of 4-(N,N-dibutylamino)benzaldehyde (Aldrich Chemical Co., Ltd.), 22.6 g of compound A-2 obtained as described above and 160 mL of dehydrated tetrahydrofuran, after which 17.5 of tert-butoxypotassium (Wako Pure Chemical Industries) and 3.2 g of 18-crown-6 (Kanto Chemical) (1.57 mol/L) were added in two divided portions. The contents of the flask were then stirred at room temperature for 200 minutes.

After reaction completion, 1 N hydrochloric acid was added to stop the reaction, then the organic phase was rinsed with water. Following phase separation, the organic phase was dried, concentrated by driving off the solvent in vacuo, and separation and purification were carried out by silica gel chromatography, yielding 22.5 g of the product. $^1$H-NMR measurement confirmed the product to be compound A-3 (see formula below).

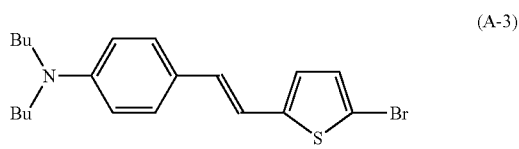

(A-3)

$^1$H-NMR (300 MHz, CDCl$_3$; TMS) δ 0.95 (t, J=7.2 Hz, —CH$_3$, 6H), 1.30-1.45 (m, —CH$_2$—, 4H), 1.55-1.70 (m, —CH$_2$—, 4H), 3.27 (m, —N—CH$_2$—, 4H), 6.59 (d, J=9.0 Hz, benzene ring hydrogen, 2H), 6.67 (d, J=3.6 Hz, thiophene ring hydrogen, 1H), 6.71 (d, J=18.0 Hz, olefin hydrogen, 1H), 6.86 (d, J=15.6 Hz, olefin hydrogen, 1H), 6.89 (d, J=3.6 Hz, thiophene ring hydrogen, 1H), 7.28 (d, J=9.0 Hz, benzene ring hydrogen, 2H).

Synthesis of Compound A-4

A 500 mL four-neck flask fitted with a condenser, a thermometer and a magnetic stirrer was charged with 12.2 g of compound A-3 obtained as described above and 400 mL of dehydrated tetrahydrofuran and cooled to −78° C. under a stream of nitrogen, following which 29.0 mL of a solution of n-butyllithium in hexane (Kanto Chemical; 1.57 mol/L) was added. After one hour of stirring at −78° C., 7.1 g of 1-formylpiperidine was added. After stirring for one hour, the temperature was raised to room temperature, then the reaction was stopped by adding 1 N hydrochloric acid. The organic phase was separated off and rinsed with water. The organic phase was dried, then concentrated by driving off the solvent in vacuo, after which separation and purification were carried out by silica gel chromatography, yielding 8.9 g of the product. $^1$H-NMR measurement confirmed the product to be compound A-4 (see formula below).

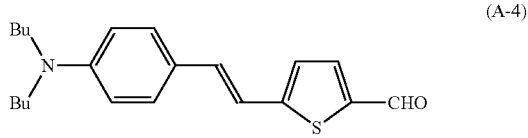

(A-4)

$^1$H-NMR (300 MHz, CDCl$_3$; TMS) δ 0.96 (t, J=6.9 Hz, —CH$_3$, 6H), 1.30-1.45 (m, —CH$_2$—, 4H), 1.55-1.70 (m, —CH$_2$—, 4H), 3.30 (m, —N—CH$_2$—, 4H), 6.60 (d, J=9.0 Hz, benzene ring hydrogen, 2H), 6.95 (d, J=15.6 Hz, olefin hydrogen, 1H), 7.03 (d, J=3.9 Hz, thiophene ring hydrogen, 1H), 7.07 (d, J=15.9 Hz, olefin hydrogen, 1H), 7.35 (d, J=9.0 Hz, benzene ring hydrogen, 2H), 7.61 (d, J=3.9 Hz, thiophene ring hydrogen, 1H), 9.79 (s, —C(=O)—H, 1H).

Synthesis of Compound A-5

A 1-liter four-neck flask fitted with a Dean-Stark trap with condenser, a thermometer and a magnetic stirrer was charged with 6.2 g of compound A-4 obtained as described above, 3.3 g of tert-butyl cyanoacetate, 1.6 g of morpholine and 600 mL of toluene, following which refluxing was carried out until the reaction reached completion. After reaction completion, the system was cooled to room temperature, then the solvent and the low-boiling reaction product were distilled off and concentrated in vacuo. Next, separation and purification were carried out by silica gel chromatography, yielding 7.6 g of the product. $^1$H-NMR measurement confirmed the product to be compound A-5 (see formula below).

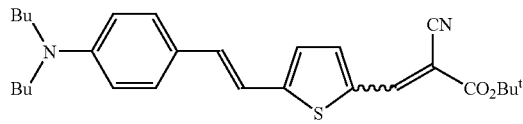

(A-5)

$^1$H-NMR (300 MHz, CDCl$_3$; TMS) δ 0.97 (t, J=7.2 Hz, —CH$_3$, 6H), 1.30-1.45 (m, —CH$_2$—, 4H), 1.50-1.70 (m, —CH$_2$—, 4H), 1.57 (s, —CH$_3$, 9H), 3.30 (t, —N—CH$_2$—, 4H), 6.61 (d, J=8.7 Hz, benzene ring hydrogen, 2H), 6.97 (d, J=18.0 Hz, olefin hydrogen, 1H), 7.00 (d, J=2.1 Hz, thiophene ring hydrogen, 1H), 7.12 (d, J=15.9 Hz, olefin hydrogen, 1H), 7.36 (d, J=8.7 Hz, benzene ring hydrogen, 2H), 7.56 (d, J=3.9 Hz, thiophene ring hydrogen, 1H), 8.14 (s, Ar—CH=(CN)COO—, 1H).

Synthesis of Compound A

A 200 mL four-neck flask fitted with a condenser, a thermometer and a magnetic stirrer was charged with 2.1 g of compound A-5 obtained as described above and 57 mL of acetic acid, following which 8 g of 48% hydrobromic acid was added and the flask contents were stirred at room temperature. Following reaction completion, the flask contents were poured into 600 mL of ion-exchanged water and extracted twice with 600 mL of methyl tert-butyl ether. The extract was then washed once with ammonia water and twice with water, and subsequently concentrated by driving off the solvents in vacuo, yielding 1.6 g of the product. $^1$H-NMR measurement confirmed the product to be a terminal amino group-containing compound (Compound A) of the invention.

$^1$H-NMR (300 MHz, DMSO-d$_6$; TMS) δ 0.92 (t, J=6.9 Hz, —CH$_3$, 6H), 1.25-1.40 (m, —CH$_2$—, 4H), 1.40-1.55 (m, —CH$_2$—, 4H), 3.33 (t, —N—CH$_2$—, 4H), 6.64 (d, J=9.0 Hz, benzene ring hydrogen, 2H), 7.13 (d, J=16.5 Hz, olefin hydrogen, 1H), 7.24 (d, J=16.5 Hz, olefin hydrogen, 1H), 7.30 (d, J=3.6 Hz, thiophene ring hydrogen, 1H), 7.46 (d, 8.4 Hz, benzene ring hydrogen, 2H), 7.89 (s, Ar—CH=(CN)COO—, 1H).

Example 2

Synthesis of Compound B (See Formula Below)

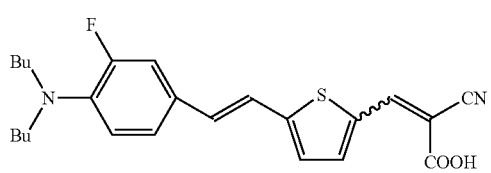

(B)

Synthesis of Compound B-1

A 500 mL four-neck flask fitted with a condenser, a thermometer and a magnetic stirrer was charged with 7 g of 3,4-difluorobenzaldehyde, 19 g of di(n-butyl)amine, 34 g of potassium carbonate, and 150 mL of anhydrous dimethylformamide as the solvent, following which the flask contents were stirred while heating at 80° C. for 10 hours under a stream of nitrogen. After cooling, the solids were removed by filtration and the filtrate was concentrated by driving off the solvent, yielding 9.3 g of the product. $^1$H-NMR measurement confirmed the product to be compound B-1 (see formula below).

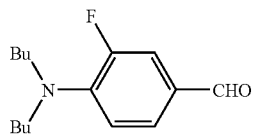

(B-1)

$^1$H-NMR (300 MHz, CDCl$_3$; TMS) δ 0.92 (t, J=7.2 Hz, —CH$_3$, 6H), 1.25-1.45 (m, —CH$_2$—, 4H), 1.50-1.65 (m, —CH$_2$—, 4H), 4.09 (t, J=6.3 Hz, N—CH$_2$—, 4H), 6.77 (t, J=8.7 Hz, benzene ring hydrogen, 1H), 7.40-7.55 (m, benzene ring hydrogen, 2H), 9.71 (d, —C(=O)—H, J=2.1 Hz, 1H).

Synthesis of Compound B

In the above-described procedure for preparing Compound A-3, aside from replacing 4-(N,N-dibutylamino)benzaldehyde with Compound B-1 synthesized as described above, Compound B was obtained by carrying out the same procedure as in Example 1.

$^1$H-NMR (300 MHz, DMSO-d$_6$, TMS) δ 0.87 (t, J=7.2 Hz, —CH$_3$, 6H), 1.28 (q, J=7.5 Hz, —CH$_2$—, 4H), 1.40-1.50 (m, —CH$_2$—, 4H), 3.10-3.40 (m, N—CH$_2$—, 4H), 6.91 (dd, J=9.0 Hz, benzene ring hydrogen, 1H), 7.16 (d, J=16.2 Hz, olefin hydrogen, 1H), 7.30-7.50 (m, benzene ring hydrogen, 2H), 7.34 (d, J=4.5 Hz, thiophene ring hydrogen, 2H), 7.41 (d, Hz, olefin hydrogen, 1H), 7.92 (d, J=4.5 Hz, thiophene ring hydrogen, 1H), 8.43 (s, Ar—CH=C(CN)COO—, 1H).

Example 3

Synthesis of Compound C (See Formula Below)

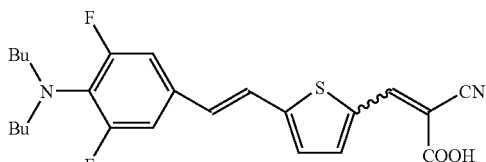

(C)

Synthesis of Compound C-1

In the above-described procedure for preparing Compound B-1, aside from replacing the 3,4-difluorobenzaldehyde with 3,4,5-trifluorobenzaldehyde, Compound C-1 (see formula below) was obtained by carrying out the same procedure.

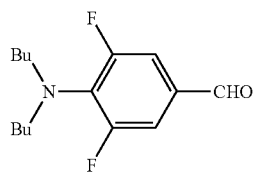

(C-1)

$^1$H-NMR (300 MHz, CDCl$_3$; TMS) δ 0.88 (t, J=7.2 Hz, —CH$_3$, 6H), 1.20-1.35 (m, —CH$_2$—, 4H), 1.40-1.55 (m, —CH$_2$—, 4H), 3.26 (t, J=7.5 Hz, N—CH$_2$—, 4H), 7.30-7.35 (m, benzene ring hydrogen, 2H), 9.77 (s, —C(═O)—H, 1H).

Synthesis of Compound C

In the above-described procedure for preparing Compound A-3, aside from replacing 4-(N,N-dibutylamino)benzaldehyde with Compound C-1 synthesized as described above, Compound C was obtained by carrying out the same procedure as in Example 1.

$^1$H-NMR (300 MHz, DMSO-d$_6$, TMS) δ 0.83 (t, J=7.2 Hz, —CH$_3$, 6H), 1.20-1.40 (m, —CH$_2$—, 8H), 3.09 (t, N—CH$_2$—, 4H), 7.19 (d, J=16.2 Hz, olefin hydrogen, 1H), 7.20-7.50 (m, benzene ring hydrogen, 2H), 7.40 (d, J=4.2 Hz, thiophene ring hydrogen, 1H), 7.59 (d, J=16.2 Hz, olefin hydrogen, 1H), 7.94 (d, J=4.2 Hz, thiophene ring hydrogen, 1H), 8.47 (s, Ar—CH═C(CN)COO—, 1H).

Example 4

Synthesis of Compound D (See Formula Below)

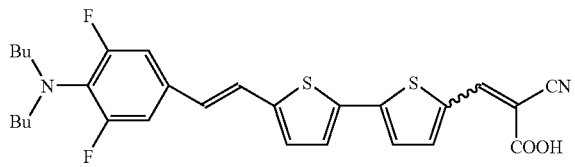

(D)

Synthesis of Compound D-1

The following ingredients were added to and dissolved in a mixed solvent composed of 60 mL of acetonitrile and 21 mL of water: 7.2 g of Compound A-2 synthesized as described above, 3.5 g of 2-thiopheneboronic acid (Wako Pure Chemical Industries), 7.0 g of sodium carbonate (Wako Pure Chemical Industries), and 0.3 g of tetrakis(triphenylphosphine)palladium (Tokyo Kasei Kogyo Co., Ltd.). The solution was stirred under heating at 80° C. for 30 hours, then treated by a standard method, yielding 3.6 g of Compound D-1 (see formula below).

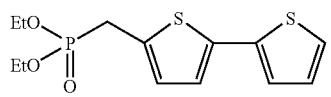

(D-1)

Synthesis of Compound D

In the above-described procedure for preparing Compound A-3, aside from replacing 4-(N,N-dibutylamino)benzaldehyde with Compound C-1 synthesized as described above and replacing Compound A-2 with Compound D-1 synthesized as described above, Compound D was obtained by carrying out the same procedure as in Example 1.

$^1$H-NMR (300 MHz, CDCl$_3$, TMS) δ 0.87 (t, J=7.0 Hz, —CH$_3$, 6H), 1.29 (m, J=7.0 Hz, —CH$_3$—, 4H), 1.42 (m, J=7.0 Hz, —CH$_2$—, 4H), 3.12 (t, J=7.4 Hz, N—CH$_2$—, 4H), 6.81 (d, J=15.9 Hz, —C═C—H, 1H), 6.94 (d, J=10.2 Hz, benzene ring hydrogen, 2H), 7.04 (d, J=4.2 Hz, thiophene ring hydrogen, 1H), 7.06 (d, J=15.9 Hz, olefin hydrogen, 1H), 7.28 (d, J=4.2 Hz, thiophene ring hydrogen, 1H), 7.34 (d, J=3.9 Hz, thiophene ring hydrogen, 1H), 7.71 (d, J=3.9 Hz, thiophene ring hydrogen, 1H), 8.30 (s, Ar—CH═C(CN)COO—, 1H).

Example 5

Synthesis of Compound E (See Formula Below)

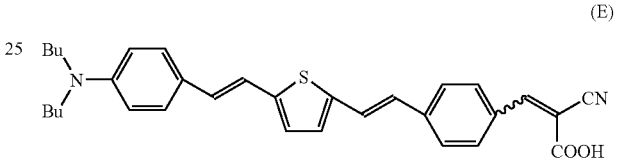

(E)

Synthesis of Compound E

Aside from replacing Compound A-1 with 4-bromobenzyl bromide (Wako Pure Chemical Industries) in the above-described procedure for preparing Compound A-2 and replacing 4-(N,N-dibutylamino)benzaldehyde with Compound A-4 in the above-described procedure for preparing Compound A-3, Compound E was obtained by carrying out the same procedure as in Example 1.

$^1$H-NMR (300 MHz, DMSO-d$_6$, TMS) δ 0.92 (t, J=7.2 Hz, —CH$_3$, 6H), 1.33 (m, —CH$_2$—, 4H), 1.51 (m, —CH$_2$—, 4H), 3.33 (m, N—CH$_2$—, 4H), 6.62 (d, J=8.4 Hz, benzene ring hydrogen, 2H), 6.84 (d, J=15.9 Hz, olefin hydrogen, 1H), 6.93 (d, J=15.6 Hz, olefin hydrogen, 1H), 7.04 (d, J=4.2 Hz, thiophene ring hydrogen, 1H), 7.11 (d, J=15.6 Hz, olefin hydrogen, 1H), 7.18 (d, J=4.2 Hz, thiophene ring hydrogen, 1H), 7.37 (d, J=8.1 Hz, benzene ring hydrogen, 2H), 7.65 (d, J=16.2 Hz, olefin hydrogen, 1H), 7.755 (d, J=7.8 Hz, benzene ring hydrogen, 2H), 8.03 (d, J=8.1 Hz, benzene ring hydrogen, 2H), 8.28 (s, Ar—CH═C(CN)COO—, 1H).

Example 6

Synthesis of Compound F (see formula below)

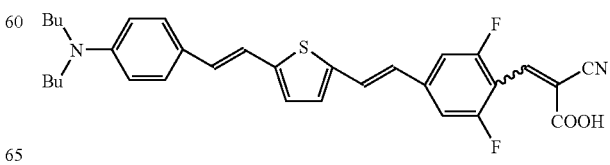

(F)

Synthesis of Compound F

Aside from replacing Compound A-1 with 3,5-difluorobenzyl bromide (Wako Pure Chemical Industries) in the above-described procedure for preparing Compound A-2 and replacing 4-(N,N-dibutylamino)benzaldehyde with Compound A-4 in the above-described procedure for preparing Compound A-3, Compound F was obtained by carrying out the same procedure as in Example 1.

$^1$H-NMR (300 MHz, DMSO-$d_6$, TMS) δ 0.92 (t, J=7.2 Hz, —CH$_3$, 6H), 1.35 (m, —CH$_2$—, 4H), 1.51 (m, —CH$_2$—, 4H), 3.32 (m, N—CH$_2$—, 4H), 6.63 (d, J=8.7 Hz, benzene ring hydrogen, 2H), (d, J=16.2 Hz, olefin hydrogen, 1H), 6.90 (d, J=16.5 Hz, olefin hydrogen, 1H), 7.06 (d, J=3.6 Hz, thiophene hydrogen, 1H), 7.12 (d, J=15.9 Hz, olefin hydrogen, 1H), (d, J=3.6 Hz, olefin hydrogen, 1H), 7.37 (d, J=8.7 Hz, benzene ring hydrogen, 2H), 7.55 (d, J=10.5 Hz, benzene ring hydrogen, 2H), 7.75 (d, J=15.9 Hz, olefin hydrogen, 1H), 8.16 (s, Ar—CH=C(CN)COO—, 1H).

Example 7

Synthesis of Compound G (See Formula Below)

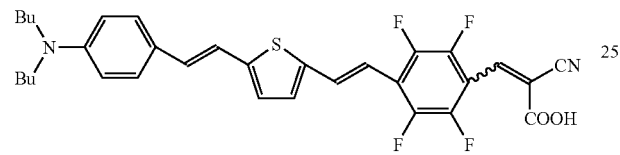

(G)

Synthesis of Compound G

Aside from replacing Compound A-1 with 2,3,5,6-tetrafluorobenzyl bromide (Wako Pure Chemical Industries) in the above-described procedure for preparing Compound A-2 and replacing 4-(N,N-dibutylamino)benzaldehyde with Compound A-4 in the above-described procedure for preparing Compound A-3, Compound G was obtained by carrying out the same procedure as in Example 1.

$^1$H-NMR (300 MHz, DMSO-$d_6$, TMS) δ 0.92 (t, J=7.2 Hz, —CH$_3$, 6H), 1.31 (m, —CH$_2$—, 4H), 1.51 (m, —CH$_2$—, 4H), 3.32 (m, N—CH$_2$—, 4H), 6.62 (d, J=8.7 Hz, benzene ring hydrogen, 2H), 6.91 (d, J=16.5 Hz, olefin hydrogen, 1H), 6.91 (d, J=16.5 Hz, olefin hydrogen, 1H), 7.03 (d, J=3.6 Hz, thiophene ring hydrogen, 1H), 7.11 (d, J=15.9 Hz, olefin hydrogen, 1H), 7.25 (d, J=3.9 Hz, thiophene ring hydrogen, 1H), 7.38 (d, J=9.0 Hz, benzene ring hydrogen, 2H), 7.79 (d, J=16.5 Hz, olefin hydrogen, 1H), 8.173 (s, Ar—CH=C(CN)COO—, 1H).

Example 8

Synthesis of Compound H (See Formula Below)

(H)

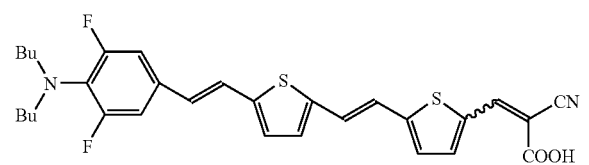

Synthesis of Compound H

Aside from replacing 4-(N,N-dibutylamino)benzaldehyde with Compound H-1 shown below, which is an intermediate in the synthesis of above-described Compound C, in the above-described procedure for preparing Compound A-3, Compound H was obtained by carrying out the same procedure as in Example 1.

$^1$H-NMR (300 MHz, DMSO-$d_6$, TMS) δ 0.83 (t, J=6.9 Hz, —CH$_3$, 6H), 1.26 (m, —CH$_2$—, 4H), 1.31 (m, —CH$_2$—, 4H), 3.06 (t, J=6.9 Hz, N—CH$_2$—, 4H), 6.88 (d, J=15.9 Hz, olefin hydrogen, 1H), 7.17 (d, J=3.9 Hz, thiophene hydrogen, 1H), 7.23 (d, J=15.9 Hz, olefin hydrogen, 1H), 7.25-7.35 (m, benzene ring hydrogen, 2H), 7.35 (d, J=3.9 Hz, thiophene ring hydrogen, 1H), 7.45 (d, J=4.5 Hz, thiophene ring hydrogen, 1H), 7.49 (d, J=4.5 Hz, olefin hydrogen, 1H), 7.93 (d, J=3.9 Hz, thiophene ring hydrogen, 1H), 8.45 (s, Ar—CH=C(CN)COO—, 1H).

(H-1)

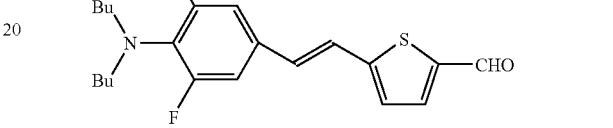

Comparative Example 1

Synthesis of Compound I (See Formula Below)

(I)

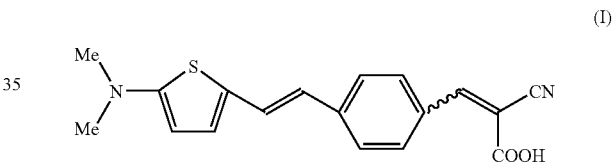

Synthesis of Compound I

Aside from not using potassium carbonate and replacing 3,4-difluorobenzaldehyde with 5-bromo-2-thiophenecarboxyaldehyde (Tokyo Kasei Kogyo), di(n-butyl)amine with dimethylamine, and anhydrous dimethylformamide with toluene in the above-described procedure for preparing Compound B-1, and aside from replacing Compound A-1 with 4-bromobenzyl bromide (Wako Pure Chemical Industries) in the above-described procedure for preparing Compound A-2, Compound I was obtained by carrying out the same procedure as in Example 2.

$^1$H-NMR (300 MHz, CDCl$_3$, TMS) δ 2.96 (s, N—CH$_3$, 6H), 5.88 (d, J=4.2 Hz, thiophene ring hydrogen, 1H), 6.49 (d, J=15.9 Hz, olefin hydrogen, 1H), 6.98 (d, J=3.9 Hz, thiophene ring hydrogen, 1H), 7.52 (d, J=15.6 Hz, olefin hydrogen, 1H), 7.62 (d, J=8.4 Hz, benzene ring hydrogen, 2H), 7.98 (d, J=8.4 Hz, benzene ring hydrogen, 2H), 8.23 (s, Ar—CH=C(CN) COO—, 1H).

Various terminal amino group-containing heterocyclic derivatives represented by general formula (1) can be synthesized by procedures similar to those used in Examples 1 to 8. For example, when the phenylene group in general formula (1) is a naphthylene, anthrylene, phenanthrylene, biphenylene or terphenylene group as in the terminal amino group-containing heterocyclic derivatives shown above in [0069], a corresponding aldehyde derivative such as 7-di-n-butylamino-2-naphthalenecarboxaldehyde may be used in place of 4-(N,N-dibutylamino)benzaldehyde in the above-described procedure for synthesizing Compound A-3. Synthesis can be carried out by a similar procedure even in cases where, in general formula (1), Y is a condensed ring such as a 2,5-thienothienylene group.

Ultraviolet-Visible Absorption Spectrum

Using acetonitrile as the solvent, solutions were prepared from Compounds A to H (the terminal amino group-containing heterocyclic derivatives of the invention synthesized in Examples 1 to 8), Compound I synthesized in Comparative Example 1, and the dye in a reference example (a ruthenium dye, produced by Solaronix SA under the brand name Ruthenium 535-bis TBA). The resulting solutions were placed in a quartz cell (path length, 1 cm), and the ultraviolet-visible absorption spectrum was measured using a spectrophotometer (JASCO Corporation; UV-Mini 1240). The results are shown in the following table.

TABLE 11

|  | Absorption maximum (nm) | Absorption edge (nm) | Molar absorption coefficient |
|---|---|---|---|
| Compound A | 515 | 687 | $4.0 \times 10^4$ |
| Compound B | 468 | 622 | $3.2 \times 10^4$ |
| Compound C | 432 | 562 | $3.6 \times 10^4$ |
| Compound D | 455 | 570 | $3.3 \times 10^4$ |
| Compound E | 471 | 678 | $2.7 \times 10^4$ |
| Compound F | 473 | 678 | $3.0 \times 10^4$ |
| Compound G | 469 | 717 | $2.0 \times 10^4$ |
| Compound H | 475 | 659 | $3.5 \times 10^4$ |
| Compound I | 476 | 725 | $1.8 \times 10^4$ |
| Reference example | 543 | 780 | $1.3 \times 10^4$ |

It is apparent from the above results that Compound A, in which a 2,5-thienylene group (an aromatic heterocyclic group) has been introduced at the Y position and a 1,4-phenylene group (an aromatic hydrocarbon group) has been introduced at the X position of the compound represented by formula 1 of the invention, when compared with Compound I in which the ring positions are reversed, has an absorption maximum wavelength at a longer wavelength and has a larger molar absorption coefficient. This suggests that configurations in which there is an aromatic hydrocarbon group at the X position and an aromatic heterocyclic group at the Y position as in the present invention most likely contribute to such effects as a shift in the absorption wavelength to a longer wavelength.

CV Measurement

Sample solutions for measurement were prepared by adding Compounds A to H (the terminal amino group-containing heterocyclic derivatives of the invention synthesized in Examples 1 to 8), Compound I synthesized in Comparative Example 1, and the dye in the above-described reference example to a supporting electrolyte solution (0.1 mol/L solution of tetra(n-butyl)ammonium tetrafluoroborate in acetonitrile). In the sample solutions, concentration of each of above described compositions is 0.001 mol/L. The working electrode, counterelectrode and reference electrode used were respectively glassy carbon, platinum wire, and Ag/Ag+ (a solution of 0.01 mol/L silver nitrate+0.1 mol/L tetrabutylammonium perchlorate in acetonitrile). After sampling 10 mL of the measurement solution and bubbling nitrogen through it for 10 minutes, CV measurement was carried out at a sweep rate of 0.1 V/s over a potential range of from 2.00 V to −1.80 V using the electrochemical system PGSTAT 12 (manufactured by Eco Chemie). The results were compared with data obtained by using ferrocene as the reference and making corrections for a normal hydrogen electrode (NHE). The results are shown in the table below.

TABLE 12

|  | One-electron oxidation potential | One-electron reduction potential |
|---|---|---|
| Compound A | +0.81 | −1.41 |
| Compound B | +0.93 | −1.32 |
| Compound C | +1.18 | −1.29 |
| Compound D | +0.92 | −1.31 |
| Compound E | +0.74 | −0.95 |
| Compound F | +0.75 | −0.69 |
| Compound G | +0.83 | −0.80 |
| Compound H | +0.90 | −0.76 |
| Compound I | +0.52 | −0.64 |
| Reference example | +0.80 | −0.80 |

In inventive compounds of formula (1), on comparing Compound A in which X is a phenylene group which is not substituted with fluorine atoms with Compound B in which X is a phenylene group substituted with a single fluorine atom and Compound C in which X is a phenylene group substituted with two fluorine atoms, as the number of fluorine atoms increases, the one-electron oxidation potential and one-electron reduction potential of the dyes can be seen to shift in each case toward the oxidation side. Moreover, on comparing Compound E with Compound F and Compound G, it is apparent that even in cases where Z has a fluorine atom, the one-electron oxidation potential shifts to the oxidation side.

These results demonstrate that the potential can be tuned by introducing fluorine atoms to suitable positions on a dye.

Photovoltaic Conversion Test

In the photovoltaic conversion test, Compounds A to H (the terminal amino group-containing heterocyclic derivatives of the invention synthesized in Examples 1 to 8), Compound I synthesized in Comparative Example 1, and the dye in the above-described reference example were used to construct photovoltaic cells, and the photovoltaic conversion efficiency was measured. The procedure used to conduct the photovoltaic conversion test is described more specifically below.

Photovoltaic Cell

FIG. 1 is a schematic view of a photovoltaic cell test specimen used in the photovoltaic conversion tests.

Transparent Electrode

A 1.1 mm thick glass substrate 1 (available from Solaronix SA) with a fluorine-doped tin oxide layer (transparent electrode layer) 2 was used.

Preparation of Titanium Oxide Paste

Titanium tetraisopropoxide (25 mL; Kishida Chemical Co., Ltd.) was added dropwise to 140 mL of an aqueous solution of nitric acid (0.1 mol/L) and stirring was carried out at 80° C. for 8 hours, thereby giving a white, semi-transparent solution. The solution was then filtered, and the resulting filtrate was treated in an autoclave at 220° C. for 12 hours. The resulting sol was concentrated with a rotary evaporator, following which distilled water was added to a titanium oxide concentration of 11 wt %.

A titanium oxide paste was then prepared by adding 22 parts by weight of P25 (titanium oxide produced by Nippon Aerosil Co., Ltd.) and 26 parts by weight of Polyethylene Glycol 20000 (Wako Pure Chemical Industries) to 1,000 parts by weight of the resulting 11 wt % titanium oxide solution and stirring.

Fabrication of Titanium Oxide Porous Electrode

A mask was created by affixing 10 µm thick mending tape to the electrically conductive side (surface of transparent electrode layer 2) of the transparent electrode, and removing a 0.5 cm square portion of the tape. Paste was coated onto the open area, following which excess paste was removed with a glass rod. After air drying, the mask was entirely removed and baking at 450° C. was carried out for 30 minutes using a oven, thereby giving a titanium oxide porous electrode having a titanium oxide porous layer 4 with an effective surface area of 0.25 cm$^2$.

Adsorption of Sensitizing Dye

Using a terminal amino group-containing heterocyclic derivative (1) synthesized in the manner described above as the sensitizing dye, this heterocyclic derivative (1) was dissolved in ethanol to make a concentration of $3.0 \times 10^{-4}$ mol/L. The titanium oxide porous layer electrode was immersed in this dye solution at room temperature for one day.

Preparation of Electrolyte Solution 5

An electrolyte solution 5 was obtained as follows.

Methoxyacetonitrile was used as the solvent to prepare an electrolyte solution containing 0.1 mol/L of lithium iodide, 0.05 mol/L of iodine, 0.5 mol/L of 4-tert-butylpyridine, and 0.6 mol/L of 1-propyl-2,3-dimethylimidazolium iodide.

A platinum layer was deposited by sputtering onto the conductive layer (transparent electrode layer 2) of the fluorine-doped tin oxide layer (transparent electrode layer) 2-bearing glass substrate 1, thereby the conductive counterelectrode (platinum electrode layer 3) was formed. Plastic film spacers 6 (Himilan 1702, produced by DuPont-Mitsui Polychemicals Co., Ltd.; thickness, 50 µm) were used as spacers between the titanium oxide porous electrode (titanium oxide porous layer 4) and the conductive counterelectrode (platinum electrode layer 3). Following cell formation, the electrolyte solution 5 was poured into the cell, after which the cell was sealed, thereby completing the fabrication of a test specimen of the photovoltaic cell. Measurement leads 7 were bonded to the edge of the conductive counterelectrode (platinum electrode layer 3) of the test specimen and to the edge of the conductive layer of the transparent electrode (transparent electrode layer 2) on the side where the titanium porous electrode has been provided.

Measurement of Conversion Efficiency

A solar simulator (K-0206, manufactured by Bunkoh-Keiki Co., Ltd.; light source: SX-150C, a 150 W xenon lamp) was combined with an air mass filter, adjusted with an actinometer to a light intensity of 100 mW/cm$^2$, and used as the light source for measurement. The I-V curve characteristics were measured with a potentiostat (Solatron 1287) while irradiating the test specimen with light. The conversion efficiency η was calculated from the following equation using the open circuit voltage (Voc), short circuit current (Jsc) and fill factor (ff) obtained from measurement of the I-V curve characteristics.

$$\eta(\%) = \frac{Voc\,(V) \times Jsc\,(mA) \times ff}{100\,(mW/cm^2) \times 0.25\,(cm^2)} \times 100$$

Using as the sensitizing dye Compounds A to D (which are terminal amino group-containing heterocyclic derivatives of the invention), Compound I synthesized in a comparative example, and the dye in the above-described reference example, photovoltaic cells were manufactured under the above-described conditions and measurements were carried out. The results are shown in the table below. The conversion efficiency η for the reference example at this time was computed to be 5.4%.

TABLE 13

|  | Short circuit current (mA/cm$^2$) | Open circuit voltage (V) | ff | Conversion efficiency (%) |
|---|---|---|---|---|
| Compound A | 8.97 | 0.64 | 0.689 | 3.96 |
| Compound B | 6.92 | 0.67 | 0.714 | 3.31 |
| Compound C | 4.17 | 0.65 | 0.717 | 1.94 |
| Compound D | 7.60 | 0.61 | 0.704 | 3.26 |
| Compound I | 1.84 | 0.47 | 0.68 | 0.66 |
| Reference example | 11.34 | 0.70 | 0.677 | 5.37 |

In the above-described method of manufacturing a photovoltaic cell, other than varying the titanium oxide paste preparation, the fabrication of the titanium oxide porous electrode, and the adsorption of the sensitizing dye in the manner indicated below, photovoltaic cells were manufactured and measurements carried out in the same way. Preparation of Titanium Oxide Paste: the Commercially available product Titanium Nanooxide T (Solaronix SA) was used.

Fabrication of Titanium Oxide Porous Electrode: Using a 90 mesh polyethylene sheet, the titanium oxide paste was applied by a screen printing technique (thickness of titanium oxide layer, about 4 to 5 µm) to the conductive surface of the transparent electrode (surface of transparent electrode layer 2) and baked at 450° C. for 30 minutes using a oven. After cooling to ambient temperature, excess titanium oxide porous layer was scraped off so as to leave an effective surface area of 0.25 cm$^2$, thereby giving a titanium oxide porous electrode having the desired titanium oxide porous layer 4.

Adsorption of Sensitizing Dye: The above titanium oxide porous electrode was immersed in a sensitizing dye solution at 40° C. for 6 hours.

Compounds A, C and E to H (which are terminal amino group-containing heterocyclic derivative of the invention), and the dye of the reference example described above were used as the sensitizing dyes. The results are presented in Table 14.

TABLE 14

|  | Short circuit current (mA/cm$^2$) | Open circuit voltage (V) | ff | Conversion efficiency (%) |
|---|---|---|---|---|
| Compound A | 8.5 | 0.618 | 0.627 | 3.29 |
| Compound C | 6.1 | 0.617 | 0.688 | 2.59 |
| Compound E | 6.4 | 0.592 | 0.625 | 2.37 |
| Compound F | 5.6 | 0.562 | 0.627 | 1.97 |
| Compound G | 4.4 | 0.576 | 0.611 | 1.55 |
| Compound H | 6.8 | 0.573 | 0.681 | 2.65 |
| Reference example | 8.8 | 0.699 | 0.637 | 3.92 |

It is apparent from these results that a comparable conversion efficiency is achieved even when terminal amino group-containing heterocyclic derivatives (1) of the invention are used instead of the ruthenium dyes that are typically preferred as sensitizing dyes in photovoltaic cells. Moreover, it is evident from a comparison of Compound A and Compound I that, although the two compounds appear at a glance to have similar structures, their photovoltaic conversion efficiencies differ dramatically. This is presumably attributable to the configuration according to the invention in which an aromatic hydrocarbon group is situated at the X position and an aromatic heterocyclic group is situated at the Y position. Even though the conversion efficiency often varies according to the balance with other components of the photovoltaic cell, because the redox potential of the inventive compounds can be tuned by fluorine atom substitution, it is possible to achieve the performance desired for the conditions under which the cell will actually be used.

INDUSTRIAL APPLICABILITY

The inventive terminal amino group-containing heterocyclic derivatives of above general formula (1) have a broad absorption band in the visible region, and are thus particularly suitable as sensitizing dyes for photovoltaic conversion in dye-sensitized photovoltaic cells. In addition to the applications mentioned in this specification, the inventive compounds may also be employed in a broad range of applications, such as nonlinear optical materials, provided they do not interfere with the actions thereof.

The invention claimed is:

1. A compound of formula (1):

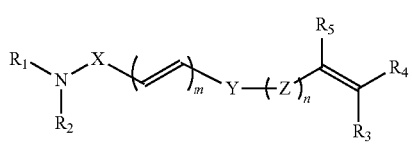

wherein
  $R_1$ and $R_2$ are each independently a $C_{1-4}$ alkyl group or a $C_{6-14}$ monovalent aromatic hydrocarbon group;
  $R_3$ is a carboxylic acid group or carboxyl group;
  $R_4$ is a cyano group;
  $R_5$ is a hydrogen atom;
  X is a phenylene, naphthylene or anthrylene group which may have one or more substituents thereon;
  Y is a 2,5-thienylene group which may have one or more substituents thereon; and
  Z is a phenylene or thienylene group which may have one or more substituents thereon, or a structure of one of the following formulae:

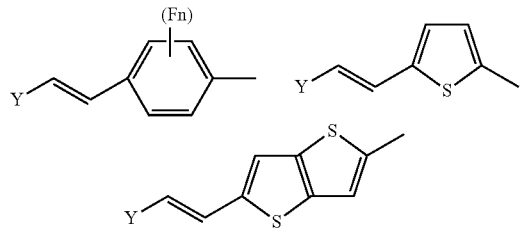

wherein the side of the structure bonding to Y in formula (1) is labeled as Y and (Fn) signifies that one or more fluorine atoms may be substituted thereon;
  m is an integer from 1 to 3;
  n is 0 or 1; and
  the double bonds in formula (1) may allow the formation of any cis-trans isomer configuration.

2. A compound of claim 1, wherein $R_1$ and $R_2$ are each independently a $C_{1-4}$ alkyl group.

3. A compound of claim 1, wherein Z is a phenylene which may have one or more substituents thereon.

4. A compound of claim 1, wherein Z is a structure of one of the following formulae:

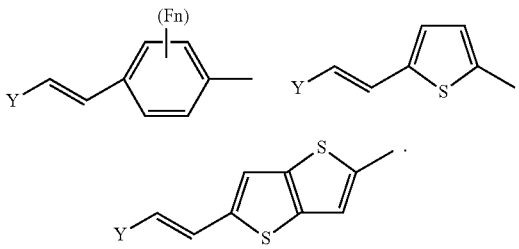

5. A compound of claim 1, having the following structure (A):

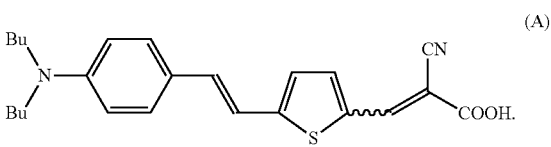

6. A compound of claim 1, selected from the group consisting of:

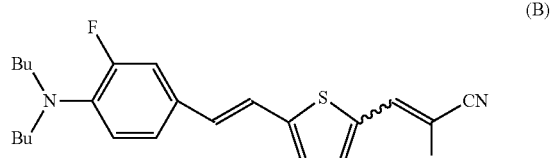

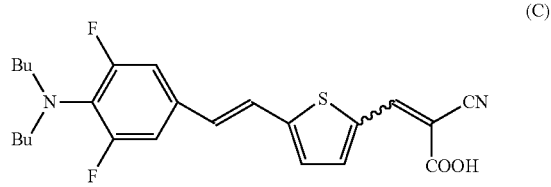

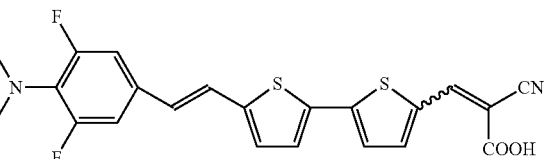

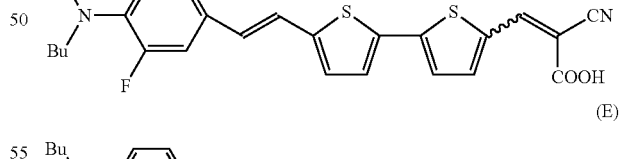

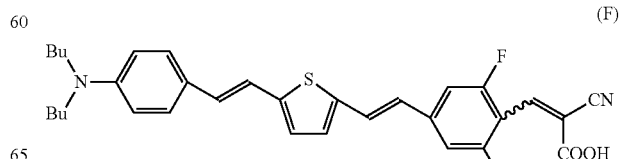

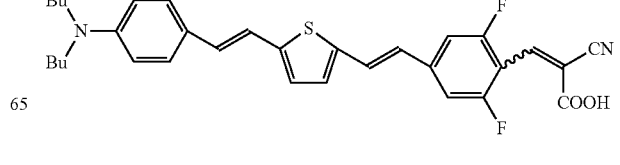

-continued

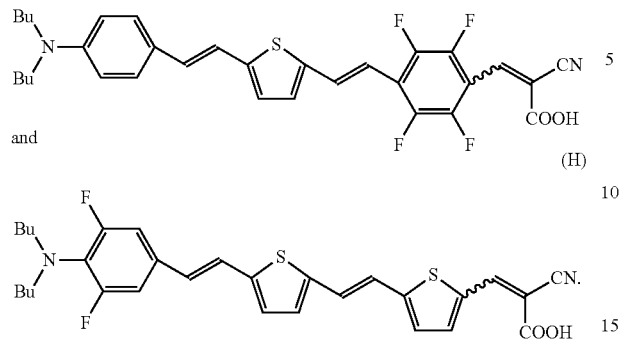

7. The compound of claim 1, wherein X is a phenylene group which may have one or more substituents thereon.

8. The compound of claim 1, wherein n is 0.

9. The compound of claim 1, wherein n is 1.

10. The compound of claim 1, wherein Z is a 2,5-thienylene group which may have one or more substituents.

11. The compound of claim 7, wherein X is a phenylene group substituted with one or more fluorine atoms.

12. A composition comprising a compound of claim 1 and a photosensitizing dye other than a compound of formula (1).

* * * * *